United States Patent
Gaddam et al.

(10) Patent No.: US 10,653,339 B2
(45) Date of Patent: May 19, 2020

(54) TIME AND FREQUENCY DOMAIN BASED ACTIVITY TRACKING SYSTEM

(71) Applicant: NXP B.V., Eindhoven (NL)

(72) Inventors: Vasanth Gaddam, Fremont, CA (US); Yifeng Zhang, San Jose, CA (US); Jie Zhang, Beijing (CN); Yuanwei Wu, Beijing (CN); Guanqing Wang, Beijing (CN)

(73) Assignee: NXP B.V., San Jose, CA (US)

( * ) Notice: Subject to any disclaimer, the term of this patent is extended or adjusted under 35 U.S.C. 154(b) by 485 days.

(21) Appl. No.: 14/681,438

(22) Filed: Apr. 8, 2015

(65) Prior Publication Data
US 2016/0296144 A1  Oct. 13, 2016

(51) Int. Cl.
| | | |
|---|---|---|
| *A61B 5/11* | (2006.01) | |
| *G01C 22/00* | (2006.01) | |
| *A61B 5/00* | (2006.01) | |
| *G01C 21/20* | (2006.01) | |

(52) U.S. Cl.
CPC .......... *A61B 5/1118* (2013.01); *A61B 5/1123* (2013.01); *A61B 5/725* (2013.01); *A61B 5/7264* (2013.01); *G01C 21/20* (2013.01); *G01C 22/006* (2013.01)

(58) Field of Classification Search
CPC ..... G01C 21/20; G01C 22/006; A61B 5/1118; A61B 5/7264; A61B 5/725; A61B 5/1123
See application file for complete search history.

(56) References Cited

U.S. PATENT DOCUMENTS

| | | | |
|---|---|---|---|
| 5,583,776 A | 12/1996 | Levi et al. | |
| 7,457,785 B1* | 11/2008 | Greitzer | G01D 1/18 706/12 |
| 7,981,058 B2 | 7/2011 | Akay | |
| 2003/0161443 A1* | 8/2003 | Xiao | G06T 11/006 378/210 |
| 2004/0203472 A1* | 10/2004 | Chien | H04B 1/30 455/68 |
| 2007/0016095 A1* | 1/2007 | Low | A61B 5/7264 600/544 |

(Continued)

OTHER PUBLICATIONS

Non Final Office Action dated Jun. 26, 2017 for U.S. Appl. No. 14/722,319 15 pages.
(Continued)

*Primary Examiner* — Vongsavanh Sengdara

(57) ABSTRACT

A method and apparatus for activity tracking based on time domain and frequency domain processing are disclosed. Embodiments according to the present invention are used to improve the accuracy of activity detection and step counting. The activity tracking starts from sample collection to generate 3-D accelerometer data. By pre-processing, the 3-D accelerometer data is calibrated and filtered. Then, the dominant component is calculated and statistical attributes or features used for activity detection are extracted. The statistical attributes are derived from time domain sensor data, frequency domain transformed data, or both. A classifier is developed using representative training data set. The activity detector determines the current activity status based on the statistical attributes and the classifier. To further refine the activity, post-processing is performed on the activity status.

16 Claims, 18 Drawing Sheets

(56) References Cited

U.S. PATENT DOCUMENTS

| | | | |
|---|---|---|---|
| 2008/0105065 A1* | 5/2008 | Lee | A61B 5/112 73/865.4 |
| 2008/0120062 A1* | 5/2008 | Lee | G01C 22/006 702/160 |
| 2008/0288200 A1 | 11/2008 | Noble | |
| 2009/0265297 A1* | 10/2009 | Misra | G06N 99/005 706/52 |
| 2010/0023307 A1* | 1/2010 | Lee | G05B 23/0254 703/7 |
| 2010/0079334 A1* | 4/2010 | Roh | G01C 21/165 342/357.29 |
| 2010/0082288 A1 | 4/2010 | Cattin et al. | |
| 2011/0065460 A1* | 3/2011 | Kimishima | G01C 25/00 455/457 |
| 2011/0077017 A1* | 3/2011 | Yu | H04L 5/0007 455/452.1 |
| 2011/0125419 A1* | 5/2011 | Bechhoefer | F03D 7/047 702/34 |
| 2013/0013249 A1 | 1/2013 | Hagiwara | |
| 2013/0029681 A1* | 1/2013 | Grokop | G01C 21/16 455/456.1 |
| 2013/0103641 A1* | 4/2013 | Rehman | G06F 3/048 707/609 |
| 2013/0158686 A1 | 6/2013 | Zhang et al. | |
| 2013/0190903 A1 | 7/2013 | Balakrishnan et al. | |
| 2013/0217979 A1* | 8/2013 | Blackadar | A61B 5/0024 600/301 |
| 2013/0311134 A1* | 11/2013 | Kordari | G01C 22/006 702/160 |
| 2014/0100465 A1* | 4/2014 | Kim | A61B 5/0402 600/509 |
| 2014/0309709 A1* | 10/2014 | Gozani | A61B 5/4809 607/46 |
| 2015/0128711 A1* | 5/2015 | Ismail | G01H 1/00 73/652 |
| 2015/0342513 A1* | 12/2015 | Wu | A61B 5/1107 600/595 |
| 2016/0029949 A1* | 2/2016 | Landesberg | A61B 5/1135 600/534 |

OTHER PUBLICATIONS

Final Office Action dated Jun. 13, 2018 for U.S. Appl. No. 14/722,319 8 pages.

* cited by examiner

TIME AND FREQUENCY DOMAIN BASED ACTIVITY TRACKING SYSTEM

CROSS-REFERENCE TO RELATED APPLICATION

This application claims the benefit of U.S. Provisional Application No. 61/985,469, filed Apr. 29, 2014, U.S. Provisional Application No. 61/985,470, filed Apr. 29, 2014 and U.S. Provisional Application No. 61/985,471, filed Apr. 29, 2014, all of them are being incorporated herein by reference.

BACKGROUND

In recent years, there has been an increasing need to use technologies to monitor health and fitness. Providing users with real-time and accurate information about their daily activities in a non-intrusive manner has become a promising approach. Using these technologies for tracking activities, users can adjust their daily activities, to meet their personal fitness goals, for example. Also, in casual and competitive sports, users want to see their performance (e.g., running speed, jump height, stride length, etc.) in real-time and make adjustments in their training routine to meet the performance goals.
The implementation of activity tracking relies on the use of sensors. The sensors may include accelerometers, gyroscopes, magnetometers, barometers, temperature sensor, etc. To allow continuous tracking of user activities, the sensors are normally worn on the user's body. These sensors can be placed on one or multiple locations on the user's body depending on the application. To be more useful, the activities are tracked continuously for a prolonged period of time.

BRIEF SUMMARY OF THE INVENTION

A method and apparatus for activity detection or activity tracking based on time domain and frequency domain processing are disclosed. Embodiments according to the present invention can be used to improve information accuracy for the activity tracking.

In one embodiment, a system for activity tracking is disclosed. The system includes a 3-D accelerometer, a pre-processor module coupled to the 3-D accelerometer, a dominant component computation unit coupled to the pre-processor module, a statistics generator module coupled to the dominant component computation unit and a classifier for detecting an activity based on outputs of the dominant component computation unit and the statistics generator module. The system may also include a post-processor that is configured to refine an output of the classifier prior to outputting a result of the classifier. The system further includes a step counter configured to output number of steps based on an output of the dominant component computation unit. The system may also include a post-processor that is configured to refine an output of the step counter prior to outputting a result of the step counter.

The statistics generator includes a first statistics module and a second statistics module. The first statistics module is configured to generate statistics based on an output of the dominant component computation unit and the second statistics module is configured to generate statistics based on an output of the pre-processor module. The pre-processor is configured to remove a direct current (DC) component in a vector sample received from the 3-D accelerometer. The dominant component computation unit is configured to determine a dominant component in the vector sample. The vector sample includes a horizontal component and a vertical component. The vertical component is proportional to a vector inner product between a mean vector of a plurality of vector samples along three axes and each dynamic vector corresponding to a first difference between each of the plurality of vector samples and the mean vector. The horizontal component is related to a norm of a second difference between the first difference and the mean vector scaled by the vertical component.

The pre-processor module may include a level normalization module, a DC notch filter and a low pass filter. The normalization module is configured to remove a gravity component from the output of the 3-D accelerometer.

In another embodiment, a non-transitory computer readable media including programming instruction which when executed by a processor performs an operation is disclosed. The operation includes pre-processing an output of a 3-D accelerometer. The pre-processing includes removing a direct current (DC) component from an output of the 3-D accelerometer. The operation further includes determining a dominant component in the output of the 3-D accelerometer after the pre-processing, wherein the output of the 3-D accelerometer includes a vertical component and a horizontal component. The vertical component is proportional to a vector inner product between a mean vector of a plurality of vector samples along three axes and each dynamic vector corresponding to a first difference between each of the plurality of vector samples and the mean vector. The horizontal component is related to a norm of a second difference between the first difference and the mean vector scaled by the vertical component. The operation also includes determining an activity type based on statistical data and the dominant component.

In some embodiments, the operation may also include determining the activity type based on a step counting based on the determining the dominant component.

In some embodiments, the statistical data includes a first statistical data generated based on the pre-processing and a second statistical data generated based on the determining the dominant component. The determining the activity type may further be based on cumulative distribution for first values of the statistical data. The cumulative distribution is divided into multiple sections associated with first values of the statistical data and second values of a plurality of statistical features of a particular activity and wherein each section corresponds to a ratio range of the first values to the second values.

In some embodiments, the multiple sections correspond to five sections and the five sections correspond to great than 0 and equal to or less than 5%, great than 5% and equal to or less than 10%, great than 10% and equal to or less than 90%, great than 90% and equal to or less than 95%, and great than 95% and equal to or less than 99%.

In yet another embodiment, a computer readable media including programming instructions which when executed by a processor performs an operation for determining an activity is disclosed. The operation includes receiving raw data from a 3-D accelerometer, filtering the raw data using a low pass filter and a high pass filter and removing a direct current (DC) component from the raw data, calculating a time domain mean value and a time domain energy of the filtered raw data, estimating dominant component in the filtered raw data and determining the activity based on the estimating and the calculating.

According to some embodiments, the method for activity detection or activity tracking is based on statistical features extracted from vector samples of a subject, a dominant component of the vector samples, or both the vector samples and the dominant component. The method comprises collecting the vector samples from a 3-D (3-dimension) accelerometer attached to a subject; computing a dominant component; calculating the statistical features; and identifying an activity class based on the statistical features. The dominant component corresponds to a vertical component or a horizontal component. The vertical component is proportional to a vector inner product between a mean vector of the vector samples along three axes and each dynamic vector corresponding to a first difference between each vector sample and the mean vector. The horizontal component is related to a norm of a second difference between the first difference and the mean vector scaled by the vertical component. The vector sample collection may be performed at a pre-defined sample rate or a dynamic rate adjusted according to a detected or predicted activity of the subject. The identifying may comprise a first and a last stage to determine the activity class. The activity class is identified in the last stage associated with a classification result of the first stage.

The method may further comprise pre-processing the vector samples before the vector samples are used for said computing the dominant component. The pre-processing may normalize the vector samples to gravity and filtering the samples. The filtering operation may remove DC (direct current) components present in the vector samples, high frequency noise or low frequency noise of the vector samples. The method may also comprise a post-processing process performed after identifying the activity class.

Each statistical feature may be selected associated with a minimum overlap on value ranges among all activities. The activity class is identified associated with a classifier. The classifier may use training data to generate a cumulative distribution plot for each statistical feature. The cumulative distribution plot may be divided into multiple sections associated with first values of each statistical features and second values of all the statistical features related to one particular activity. Each section corresponds to a ratio range of the first values to the second values. The multiple sections may correspond to five sections. The five sections may correspond to (0-5%], (5%-10%], (10%-90%], (90%-95%] and (95-99%].

Each of the statistical features may be calculated based on individual axis accelerometer data of the vector samples, combined accelerometer data of the vector samples, the vertical component or the horizontal component. The statistical features may comprise a time domain mean value of the vector samples, a variance of the dominant component and time domain energy of vector samples without the DC components.

The activity class may be identified associated with a highest value among multiple metrics of all activities. Each metric is determined by combining values of each statistical feature with corresponding section dependent weights. The section dependent weights are pre-determined or dynamically adjusted.

According to another embodiment, the method for activity detection or activity tracking is based on statistical features extracted from frequency-domain data of vector samples only. The statistical features may also be extracted from frequency-domain data together with time-domain data of the vector samples, a dominant component of the vector samples, or both. The method comprises collecting vector samples from a 3-D (3-dimension) accelerometer attached to a subject; transforming the vector samples to frequency-domain samples; calculating the statistical features associated with the frequency-domain samples; identifying an activity class based on the statistical features.

The method may also comprise pre-processing the vector samples, computing a dominant component before the transformation; and a post-processing process after said identifying the activity class.

The frequency-domain samples may be calculated based on combined accelerometer data of the vector samples, the vertical component or the horizontal component. At least one of the statistical features may be selected from a peak, a location of the peak and sub-band frequency domain energy of the frequency domain samples. The statistical features may comprise a time domain mean value, a variance of the dominant component, time domain energy of the vector samples without the DC components, and sub-band frequency-domain energy of the frequency-domain samples.

According to one embodiment of the present invention, the apparatus for activity detection or activity tracking comprises an accelerometer for collecting vector samples of a subject, a computation unit for computing a dominant component, one or more modules for calculating statistical features, and a classifier for identifying an activity class based on the statistical features. The statistical features are calculated from the dominant component, the vector samples, or both.

The dominant component is computed based on the vector samples. The dominant component corresponds to a vertical component or a horizontal component based on the sensor location on the body (e.g., foot, wrist, waist). The vertical component is proportional to a vector inner product between a mean vector of the vector samples along three axes and each dynamic vector corresponding to a first difference between each vector sample and the mean vector. The horizontal component is related to a norm of a second difference between the first difference and the mean vector scaled by the vertical component.

According to another embodiment of the present invention, the apparatus for activity detection or activity tracking comprises a 3-D accelerometer used to collect vector samples of a subject, a first module configured to transform the vector samples into frequency-domain samples, one or more second modules configured to calculate statistical features associated with the frequency-domain samples, and a classifier configured to identify an activity class based on the statistical features.

The apparatus may further comprise a pre-processing module coupled to the 3-D accelerometer, wherein the pre-processing module is configured to pre-processing the vector samples before being used to compute the dominant component or before being transformed to frequency-domain samples. The apparatus may further comprise a post-processing module coupled to the classifier. The post-processing module may be configured to post-processing data associated with the activity class.

DETAILED DESCRIPTION OF THE INVENTION

Figure 1:
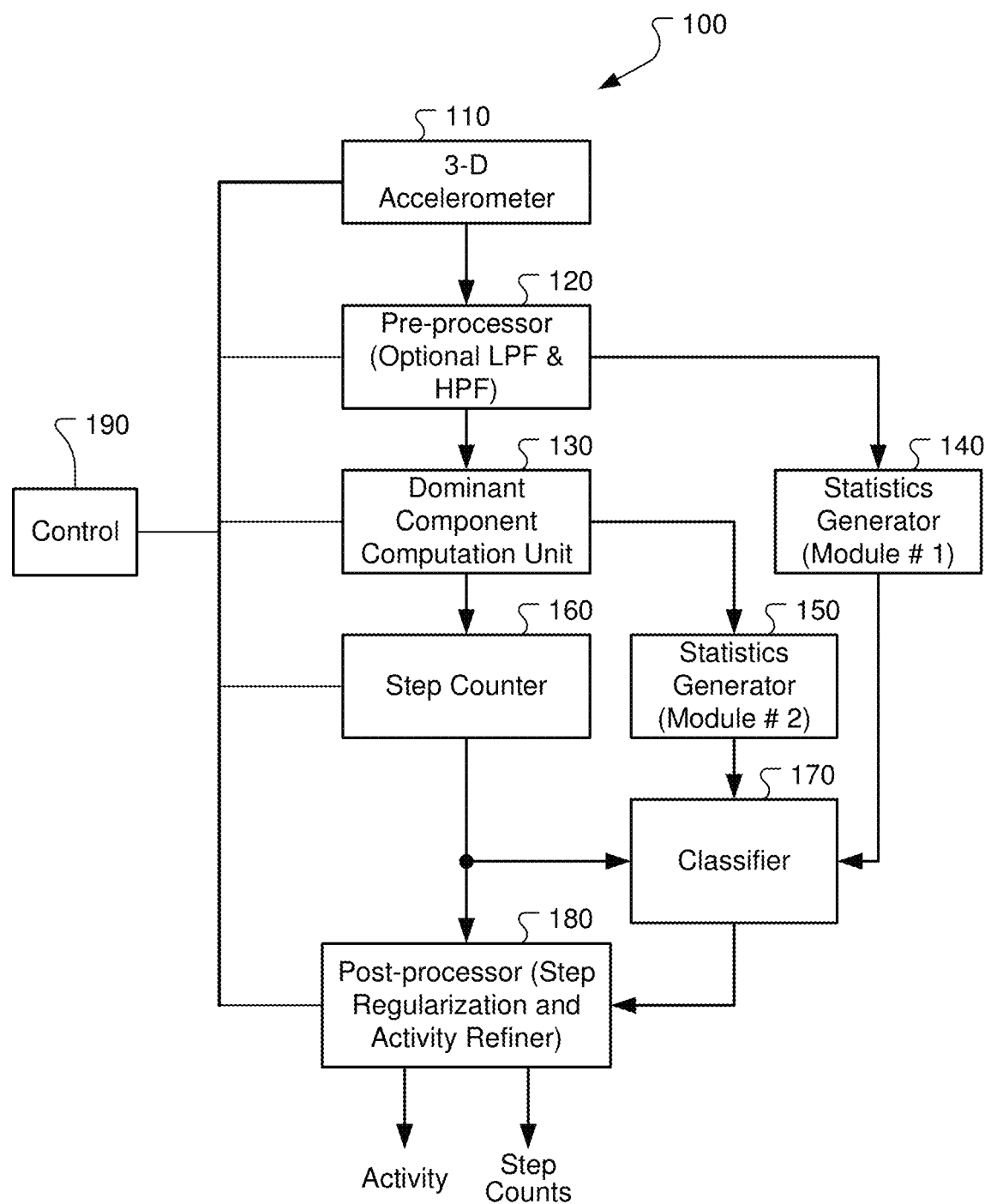
FIG. 1 illustrates an exemplary diagram of the tracking system for estimating activity and step count according to one embodiment of the present invention.

There are many different types of sensors that can be employed to collect activity data. For more refined results, the sensors should be used for a prolong period of time. Therefore, it is imperative that the sensors be lightweight and offer a reasonably long battery life. The embodiments described herein include an activity monitoring device that contains one more sensors. Generally speaking, micro electro-mechanical (MEMS) sensors are suitable to be included in the activity monitoring device. MEMS sensors are lightweight and use less energy to operate. Other types of sensors that are light weight and offer energy efficiency may also be suitable to be used in the activity monitoring device.

In addition to activity monitoring, the systems and methods described herein can be used to enable context awareness in other devices such as mobile communication or computing devices to improve user experience.

The systems and methods described herein provides sampling the data from sensors and processing the sampled data to estimate a user's activity. The process of estimation may employ various forms of algorithms. Various embodiments described herein addresses several limitations and deficiencies currently being employed in activity monitoring products. First the processing of the sensors data is normally done in the time domain that may limit the accuracy and reliability of the result when the time domain sensor data are noisy or difficult to be classified into different activities in some cases. Another limitation of current activity tracking is that the optimization of the activity tracking is normally done for one performance metric only. However, in real world applications it is desirable to optimize for multiple performance metrics (such as power consumption, accuracy, latency). Yet another typical limitation of the current activity tracking methods is using a fixed data sampling rate, which can lead to insufficient sampling for fast changing activities or unnecessary power consumption when rate is higher than needed.

In one embodiment, in conjunction with a processing system, an accelerometer is used to determine the activity and the step count of a user. If the accelerometer is placed at a fixed location and orientation on the body then a one-dimensional accelerometer is sufficient to determine the user activity. A 3-D accelerometer can be used to overcome the limitation of the fixed location and orientation. A 3-D accelerometer consists of three accelerometer elements, each sensing in perpendicular direction to the other two elements. In some embodiments, additional sensors such as gyros and magnetometers can also be used to improve accuracy of the user's activity monitoring.

There exist a number of solutions that addresses the need of providing information to some extent. However, these solutions are not optimal for all performance metrics (such as accuracy, power consumption, latency, etc.) and are typically aimed at optimization of one metric based on the application requirement. Most of the solutions usually use time domain approaches in order to reduce computational requirements.

In accordance with one or more embodiments, a 3-D accelerometer is used in the activity tracker or monitor described herein to identify distinct user activities and also to collection information such as number of steps the user has walked irrespective of the orientation and location of the activity tracker on the body of the user. It should be noted that the term "user" used herein may also include non-human objects whose activities or movements need to be tracked. It should also be noted that the output of the activity tracker may also be used to derive auxiliary data such as calories expended, distance travelled, speed, jump height, etc.

FIG. 1 shows a top-level schematic of the activity tracking system 100 combining time domain and frequency domain processing. The activity tracking system 100 consists of a 3-D accelerometer 110 and one or more signal processing modules to process the accelerometer data and extract determine the activity of a user who is using the activity tracking system 100. In one embodiment, a classifier 170 is included to process the pre-processed data based on the output of one or more statistics generators 140, 150 to determine the user's activity. In other embodiments, the classifier 170 may be placed in an external device such as a mobile phone device.

A pre-processor 120 is included to normalize the data provided by the 3-D accelerometer 110. The pre-processing may include removing gravitational component. In other embodiments, the pre-processing may also include removing noise from the data received from the 3-D accelerometer 110. In some embodiments, the pre-processor 120 may include a low pass filter (LPF). In other embodiments, the pre-processor 120 may include a high pass filter (HPF). And in some other embodiments, both LPF and HPF may be included. The pre-processor 120 may also perform calibration of the input data based on a preset criteria.

A dominant component computation unit 130 is included to determine a dominant component in the data provided by the 3-D accelerometer 110. The determination of the dominant component may include computing a vertical and a horizontal component in the data received from the 3-D accelerometer 110, and then determining which one of the horizontal and the vertical components is the dominant component. For example and for the ease of understanding only, if the activity tracker system 100 is mounted in a shoe, the horizontal component may be the dominant data whereas if the activity tracker system 100 is mounted on the arm, the vertical component may be the dominant data for the purpose of determining the activity.

One or more statistics generator modules 140, 150 may be included to extract statistical attributes from previous data captured from the dominant component computation unit 130 and the pre-processor 120. The statistics data may also be inputted to the statistics generators 140, 150 from an external source as for example, the activity tracker system 100 may be preconfigured with sample statistical data. Over the period of use, the externally inputted statistical data may be refined based on the data collected from the pre-processor 120. In some embodiments, the functionality of the two statistics generators 140, 150 may be combined in one single unit.

In some embodiments, the activity detection is based on a time domain sensor data, a frequency domain transformed data, or both. According to one embodiment, the activity is determined based on features derived from time domain sensor data including a vertical component or a horizontal component. In another embodiment, the activity detection is based on frequency domain transformed data. In some embodiments, time domain (TD) and frequency domain (FD) data processing can also be combined for more accurate activity tracking. It should be noted that at least some of the modules described herein may be implemented in software or hardware.

In some embodiments, a sample data is selected in the analog output of the 3-D accelerometer 110. For example, a sample may include a data within a selected time slot or a selected length. The sampled data may then be split into blocks of sub-samples (e.g., example 3 or 4 seconds long snapshots). A dominant component is determined in the sampled blocks. The dominant component may be Horizontal or Vertical component. One or more attributes or features are computed in each of the sampled blocks. Examples of the extraction of attributes may include computing mean, variance, and energy of the time domain signal. In another example, the extraction of attributes may include one or more of computing mean, variance, signal energy of the previously determined dominant component. In other examples, peak value, location, sub-band energy of the frequency domain signal may be computed. Computing features or attributes on the dominant component in the output of the 3-D accelerometer is beneficial because calculations on the dominant component to determine an activity provide better identification of the activity compared to performing the calculations on the raw data provided by the 3-D accelerometer 110 because the orientation and/or placement of the 3-D accelerometer 110 may skew activity detection without first finding the dominant component in the raw data provided by the 3-D accelerometer.

The statistics generators 140 or 150 can be used to perform frequency domain transformation and generate statistical attributes based on the frequency domain transformed data. The classifier 170 determines the current activity status based on the generated statistical attributes. In some embodiments, the step counter 160 uses the output of the dominant component unit 130 to estimate step count. Also in some embodiments, a post-processor 180 may be used to further regularize the estimated step count and refine the activity status calculated by the classifier 170. In some embodiments, the statistics generators 140 and 150 may be combined in one module. In one embodiment, the statistics generators 140 and 150 may perform frequency domain transformation on the data received from the pre-processor 120 or the dominant component computation unit 130.

The control module 190 is used for system initialization, configuration, monitoring and a plurality of control functions. The control module 190 provides control signals or commands to one or more processing modules that are depicted in FIG. 1. The control module 190 may also provide data processing support to one or more processing modules depicted in FIG. 1. The control module 190 can be implemented based on a CPU (central processing unit), one or more microcontroller, individual embedded controllers associated with processing modules, or a combination thereof. In some embodiment, the control module 190 may implemented using logic circuits for performing predefined specific operations. The control module 190 may also be programmable via software, firmware or micro codes.

The control module 190 can be configured to manage reliability, latency and battery life trade-offs. Control algorithm requires a number of parameters that can be configured automatically depending on certain operating conditions. To improve the performance, the control module 190 may be programmed to perform additional processing based on the position of the accelerometer 110. For example, the control module 190 may change some of the thresholds used in the classifier 170 and the step counter 160 based on the position of the 3-D accelerometer 110.

In some embodiments, the control module 190 can also be used to control the operation of the 3-D accelerometer. Typically, the 3-D accelerometer provides analog data, which is sampled along X-axis, Y-axis and Z-axis at a pre-defined sampling rate, preferably using an analog to digital converter, to produce digital output. The sampling rate can be adjusted upward or downward dynamically based on detected or predicted activity. For example, when slow changes in activity are detected, the sampling rate of the analog to digital converter may be reduced, to save battery power without compromising the accuracy of the results. The sample rate is increased back to the original rate when enhanced activity is detected.

In one embodiment, the activity tracking system 100 may include a switch which is configured to trigger a "sleep mode". When the activity tracking system 100 is transitioned into the "sleep mode", the sampling rate is reduced to a predefined low value. In another embodiment, the control module 190 may be configured to transition the activity tracking system 100 in the "sleep mode" based on the output of at least one of the step counter 160 and the classifier 170.

Figure 2:
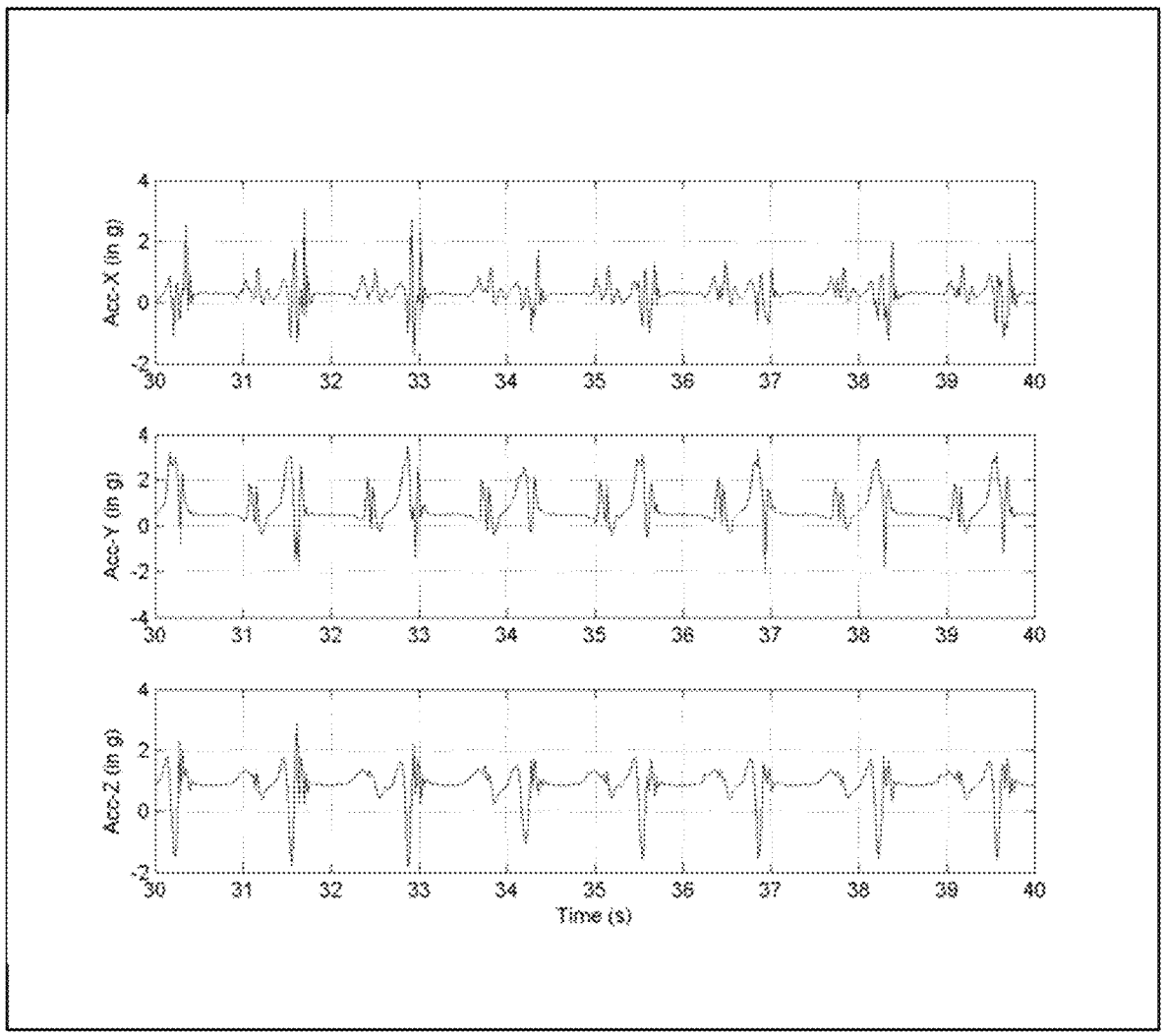
FIG. 2 illustrates an example of 3-D accelerometer data from a sensor placed on one shoe for walking activity.
Figure 3:
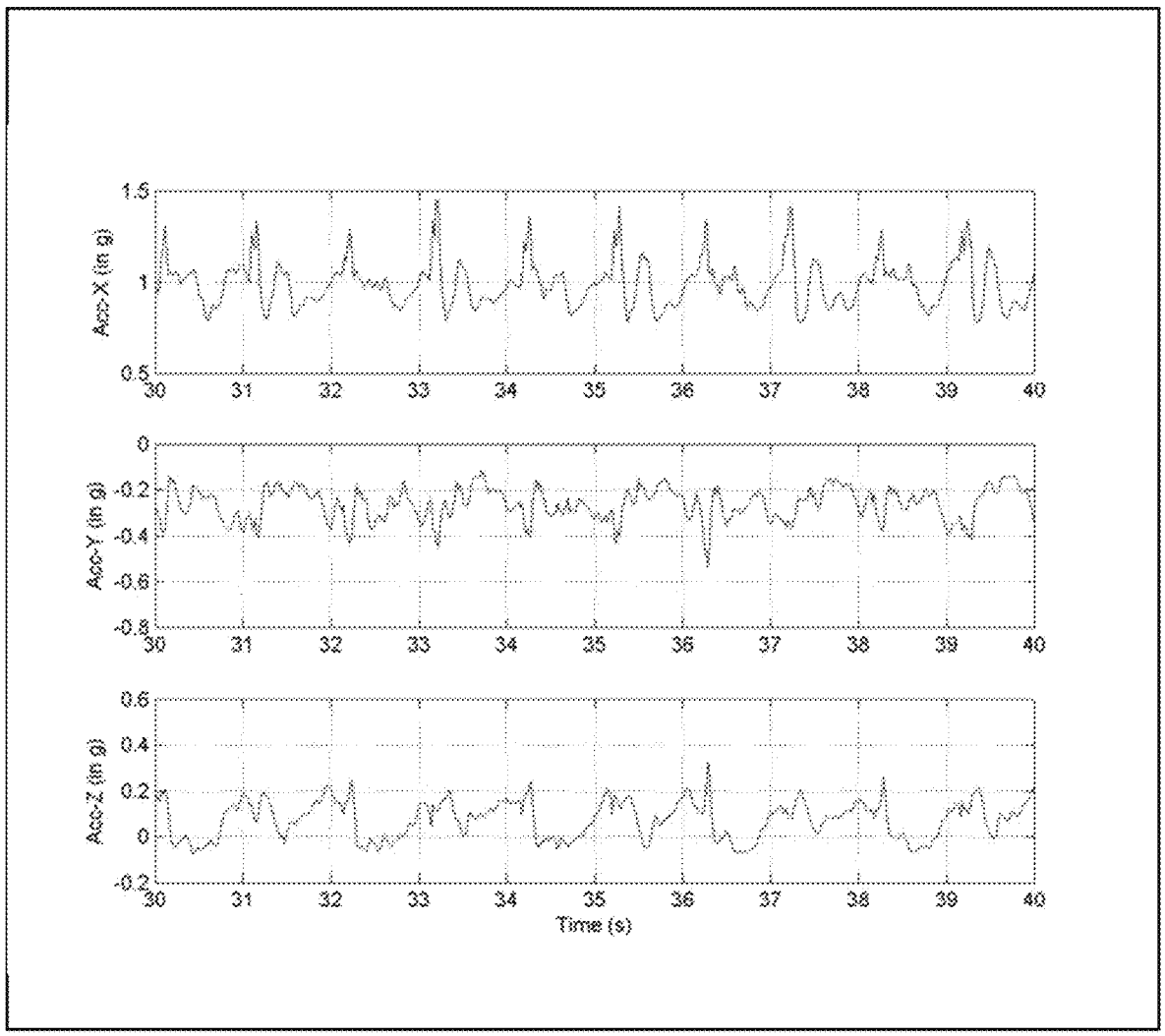
FIG. 3 illustrates an example of 3-D accelerometer data from a sensor placed on one wrist for walking activity.
Figure 4:
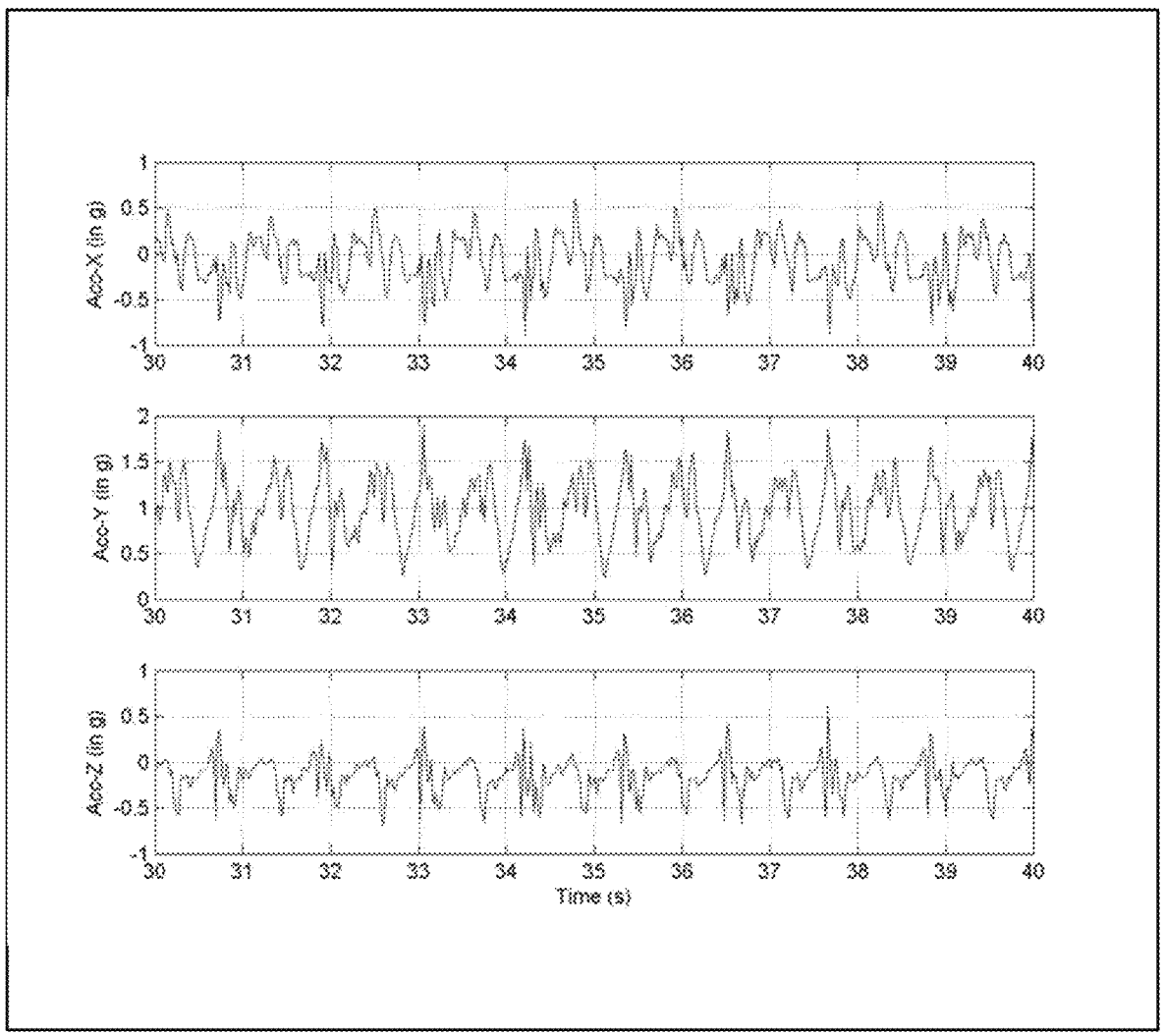
FIG. 4 illustrates an example of 3-D accelerometer data from a sensor placed on the waist for walking activity.

For the purpose of easy understanding of the systems and method described herein, the following paragraphs uses non-limiting examples. For activity tracking, the 3-D accelerometer 110 can be placed on one shoe, one wrist, the waist of the user, etc. FIG. 2, FIG. 3 and FIG. 4 show snapshots of the 3-D accelerometer data in the same 10 seconds with different sensor placements for the same user. Each snapshot of 3-D accelerometer data is from one sensor used for tracking user activity. FIG. 2 illustrates a snapshot of 10 seconds 3-D data from the sensor placed on one shoe. FIG. 3 shows the data from the sensor placed on one wrist and FIG. 4 shows the data from the sensor placed on the waist of the user. As can be observed, there is a significant variation in the data from one sensor location to another sensor location, although the overall trends seem to be similar.

A pre-processor is used for calibration to reduce the influence of the sensor placement. In the pre-processor, the accelerometer data is first normalized to g (i.e. acceleration due to gravity, which approximates to 9.8 m/s$^2$) and is made independent of the sensor. Then, some filtering operation follows the normalization process to reduce the noise of the signal. In particular, a direct current (DC) notch filter is used to remove, if necessary, the DC component present in each of the three axis accelerometer data. A low pass filter (LPF) can also be used to suppress high frequency components, as most of the activity information is present in frequency components below 5 Hz while high frequency components typically correspond to noise. A low order LPF is used to reduce computational requirements.

Figure 5:
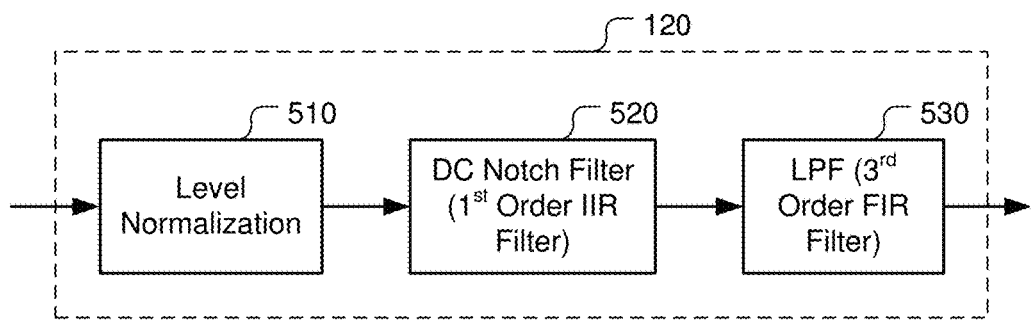
FIG. 5 illustrates an exemplary block diagram of the pre-processor.

FIG. 5 shows an example of pre-processor 120. The accelerometer data is normalized by level normalization 510. Then, a DC notch filter 520 and a LPF 530 process the normalized signal. In this example, a first order IIR (infinite impulse response) filter is used as a DC notch filter and a third order FIR (finite impulse response) filter is used as the LPF 530.

Dominant component computation 130 is used to extract step information, such as vertical and horizontal components for step counting. As the sensor position is not known a priori, the 3-D data is combined in order to extract the step information. According to one embodiment of the present invention, the 3-D data is projected along vertical axis and horizontal axis for calculating the vertical and horizontal components. This will make the data independent of the sensor orientation and therefore can be used with different sensor placement options by simple parameter tuning.

Data $\overline{A}=(A_x, A_y, A_z)$ denotes the pre-processed 3-D accelerometer data at a given sample instant.

The mean along the three axes $\overline{m}$ is given by:

$$\overline{m}=(m_x, m_y, m_z).$$

Then the dynamic component of the accelerometer data $\overline{D}$ can be generated using the following equation:

$$\overline{D}=(A_x-m_x, A_y-m_y, A_z-m_z).$$

The projection of the dynamic component along the vertical component direction is given by the vector inner product of $\overline{D}$ and $\overline{m}$, which is described by:

$$V = \overline{D} \cdot \frac{\overline{m}}{\|\overline{m}\|}.$$

The horizontal component can be obtained by projecting the dynamic component along the horizontal component direction, which can be described as:

$$H=\|\overline{D}-V\overline{m}\|.$$

For normal activities, the estimate of vertical component V, which is independent of sensor orientation, includes useful information and can be used to determine the step count. In this case, the vertical component is taken as the dominant component. In some instances, particularly for certain sensor positions, the horizontal component (also referred to as orthogonal component) rather than the vertical component will provide more useful information. Then the horizontal component is considered to be the dominant component.

Figure 6:
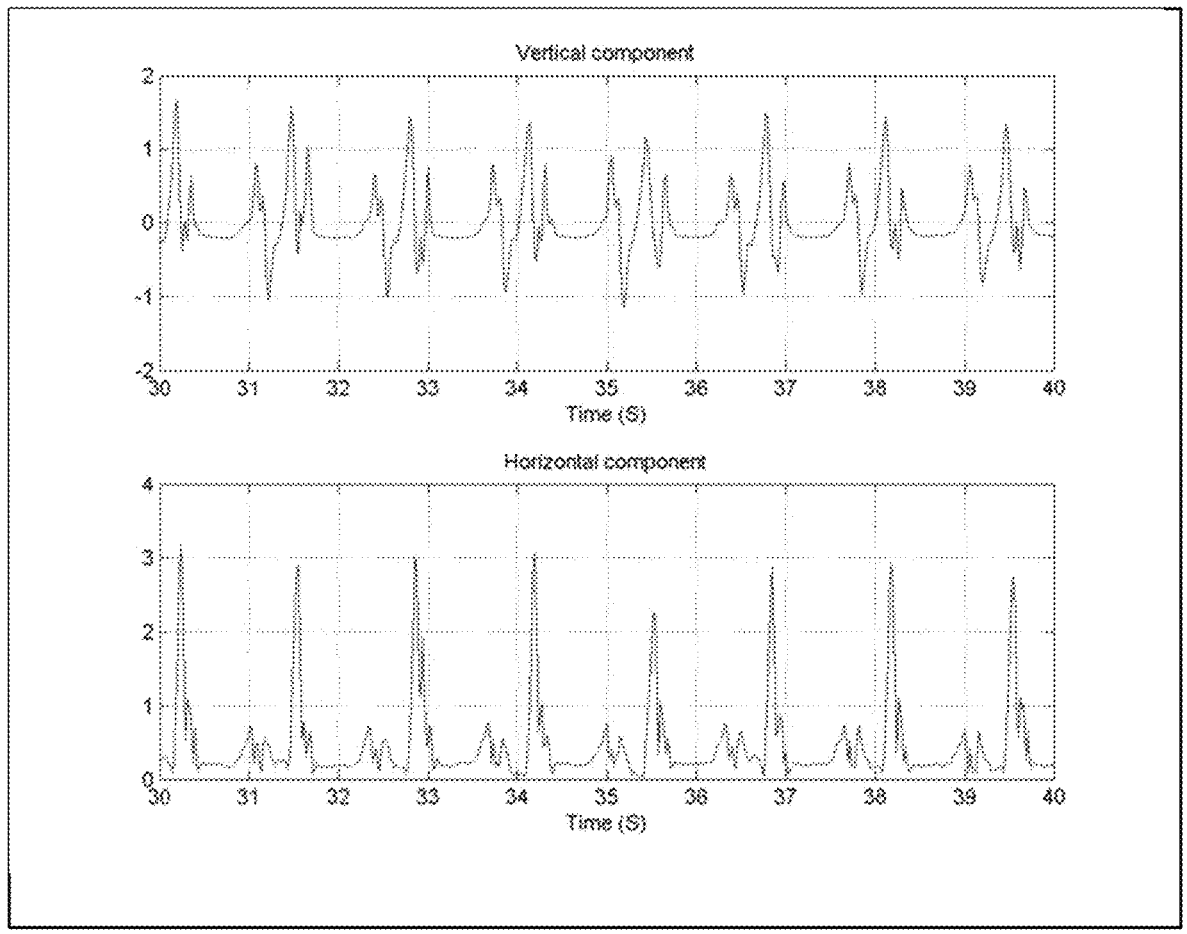
FIG. 6 illustrates an example of vertical and horizontal component estimated from the 3-D accelerometer data obtained by the sensor placed on the shoe.
Figure 7:
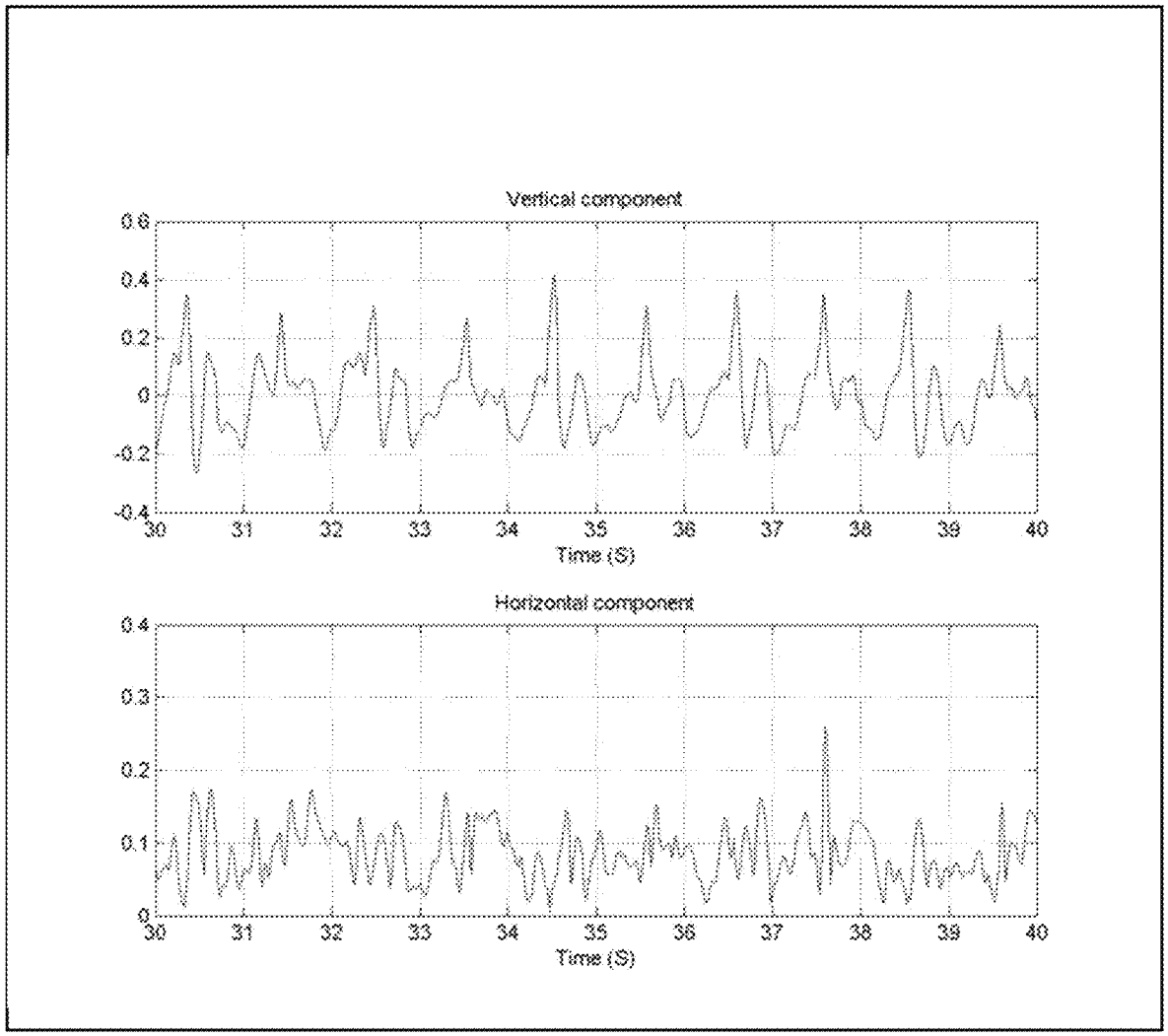
FIG. 7 illustrates an example of vertical and horizontal component estimated from the 3-D accelerometer data obtained by the sensor placed on the wrist.
Figure 8:
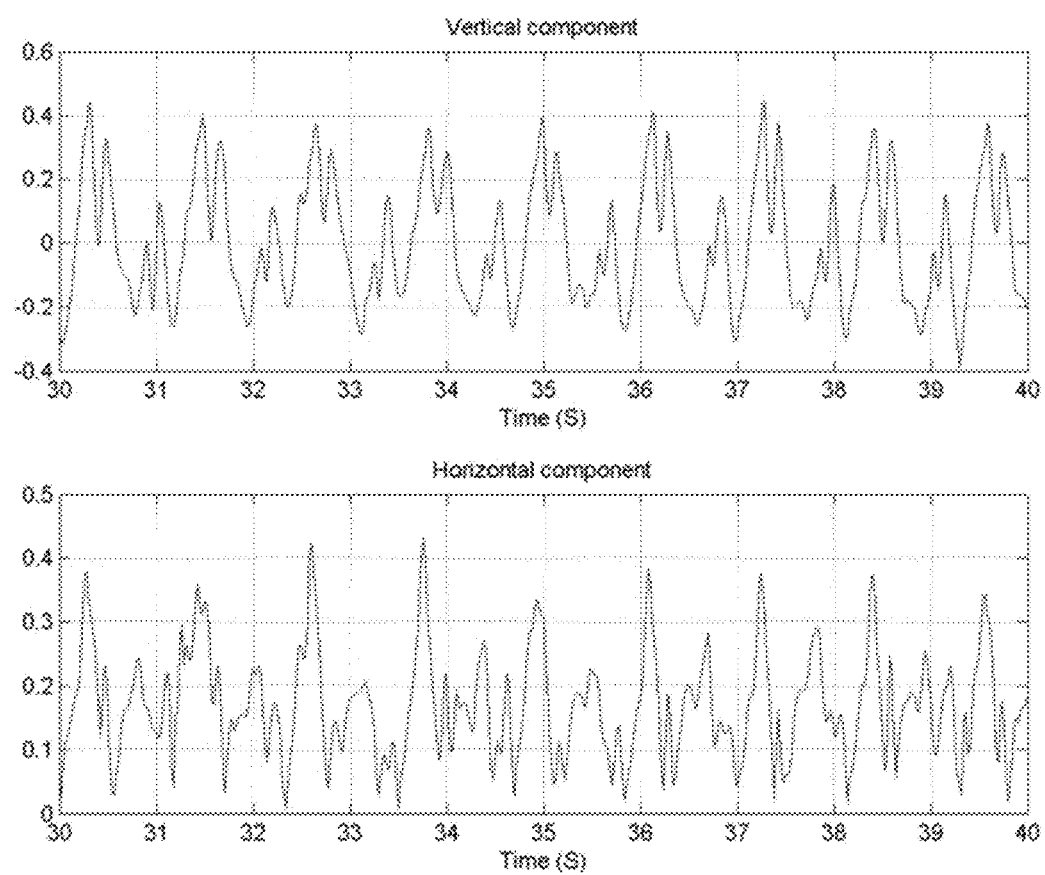
FIG. 8 illustrates an example of vertical and horizontal component estimated from the 3-D accelerometer data obtained by the sensor placed on the waist.

FIG. 6, FIG. 7 and FIG. 8 illustrate the vertical and horizontal component estimates from the 3-D accelerometer data shown in FIG. 2, FIG. 3 and FIG. 4 respectively. It can be observed from the plots that when the sensor is placed on one shoe the horizontal component has well-defined pattern compared to the vertical component. On the other hand, when then sensor is placed either on one wrist or the waist, the vertical component has well-defined pattern compared to the horizontal component.

The output of each sensor represents a sampled version of the acceleration along the three orthogonal axes. In order to determine the user activity based on the 3D accelerometer data, some attributes (or features) are derived from this data. The attributes help in compactly representing the data and as a result it is easier or manageable to generate the classifier based on the training data. Also, it is more computationally efficient to use the attributes from the test data, compared to using the raw data, to determine the user activity.

According to the embodiment, the activity detection is based on the statistical attributes derived from the time domain sensor data. The attributes derived from the time domain sensor data are selected from three sets. One set is the attributes derived from the individual axis accelerometer data; another set is the attributes calculated from the combined accelerometer data; and the third set is the attributes derived from the vertical and horizontal components.

A number of time domain attributes are extracted from the 3D accelerometer data. Data A(n) denotes the combined accelerometer data, which is described by:

$$A(n)=|A_x(n)|+|A_y(n)|+|A_z(n)|.$$

The attributes derived from the individual axis accelerometer data are described by the following formulas. The mean $m_k$, variance $\text{var}_k$, peak $p_k$ and peak to average ratio $\text{PAR}_k$ of the individual axis accelerometer data are described by:

$$m_k = \frac{1}{N}\sum_{n=1}^{N} A_k(n),$$

$$\text{var}_k = \frac{1}{N}\sum_{n=1}^{N} (A_k(n)-m_k)^2,$$

$$p_k = \max_{1\le n\le N}(A_k(n)), \text{ and}$$

$$\text{PAR}_k = \frac{p_k}{m_k}.$$

where k can be used to denote x, y or z axis. The mean, variance, peak and peak to average ratio of magnitudes of the individual axis accelerometer data are given by the following formulas respectively:

$$\overline{m}_k = \frac{1}{N}\sum_{n=1}^{N} |A_k(n)|,$$

$$\overline{\text{var}}_k = \frac{1}{N}\sum_{n=1}^{N} (|A_k(n)|-\overline{m}_k)^2,$$

$$\overline{p}_k = \max_{1\le n\le N}(|A_k(n)|), \text{ and}$$

-continued $$\overline{par}_k = \frac{\overline{p}_k}{\overline{m}_k}.$$

The attributes derived from the combined accelerometer data are computed based on the combined data of the three axes. The mean, variance, peak and peak to average ratio of combined accelerometer data are denoted as $\ddot{m}$, $\ddot{var}$, $\ddot{p}$ and $\ddot{PAR}$ respectively and given by:

$$\ddot{m}_k = \frac{1}{N}\sum_{n=1}^{N} A(n),$$

$$\ddot{var} = \frac{1}{N}\sum_{n=1}^{N} (A(n) - \ddot{m})^2,$$

$$\ddot{p} = \max_{1 \le n \le N}(A(n)), \text{ and}$$

$$\ddot{PAR} = \frac{\ddot{p}}{\ddot{m}}.$$

The time domain energy of the combined accelerometer data is described by:

$$E_{TD} = \frac{1}{N}\sum_{n=1}^{N}(A(n))^2.$$

The attributes derived from the vertical and horizontal components are computed by the following formulas. The mean of vertical component is simply an average value of vertical component described by:

$$m_v = \frac{1}{N}\sum_{n=1}^{N} V(n).$$

The mean of horizontal component is an average value of horizontal component described by:

$$m_h = \frac{1}{N}\sum_{n=1}^{N} H(n).$$

The variance of vertical component $var_v$ or the variance of horizontal component $var_h$ is an average value of the square of the difference between the vertical or horizontal component and the corresponding mean described by:

$$var_v = \frac{1}{N}\sum_{n=1}^{N}(V(n) - m_v)^2, \text{ and}$$

$$var_h = \frac{1}{N}\sum_{n=1}^{N}(H(n) - m_h)^2.$$

In another embodiment, frequency domain attributes are used to detect activities. Frequency domain attributes are calculated based on the frequency domain transformation $\mathcal{A}$. When the data A(n) is used in the frequency domain module, the frequency domain transformation is described by:

$$\mathcal{A}(k) = DFT(A(n)) = \frac{1}{N}\sum_{n=1}^{N} A(n)e^{-j2\pi k(n-1)/N},$$

where k=0 to N−1. The attributes derived from frequency domain transformed data include the peak of frequency domain transformed data, the location of the peak of the frequency domain transformed data and the sub-band frequency domain energy. The peak of frequency domain transformed data is the max value of the frequency domain transformation described by $$P = \max_{1 \le k \le N}(\mathcal{A}(k))$$

The location of the peak of the frequency domain transformed data is given by:

$$L = (\mathcal{A}(k) = P)_{k=1 \text{ to } N/2}$$

The sub-band frequency domain energy is a sum value of the squared data described by:

$$E_{FD} = \Sigma_{k=k_{init}}^{k=k_{final}}(\mathcal{A}(k))^2,$$

where $k_{init}$ and $k_{final}$ represents the initial and final frequency components of interest.

In another embodiment, the vertical component V(n) or the horizontal component H(n) is used to extract statistical attributes instead of A(n) in the frequency domain module. Then, the frequency domain attributes are calculated by using V(n) or H(n).

According to one embodiment of the present invention, the activity detector and the step counter share the same resource. This would enable reuse of some of the computations in the frequency domain.

In the example, the classifier 170 and the step counter 160 operate independently on the 3-D accelerometer data. Hence, in some instances the outputs of the classifier 170 and the step counter 160 may be in conflict. For example, the classifier 170 could indicate that the user is idle while the step counter 160 could output non-zero number of steps. This situation may occur when the step counter 160 does not use a minimum threshold to check for the signal level. Therefore, post-processing is performed to combine the information from the classifier 170 and the step counter 160 to minimize errors. In this example, the post-processing steps use information about normal human behavior to refine the output.

In some embodiments, to obtain the representative captured data, a data logging exercise is performed with several users performing multiple activities such as walking, running, sitting, standing, walking up/down stairs, jumping, etc. The representative captured data is pre-processed by the method as shown in FIG. 5 and the attributes are extracted from the 3-D data obtained from generate statistics modules (#1 and #2), and the step counter module 160 as shown in FIG. 1. The attributes together with the class information are stored in a database. The attributes derived from the training data are analyzed to check the suitability of each attribute for reliably identifying the class.

WEKA (Waikato environment for knowledge analysis) software package can be used to derive the classifier. The software package provides multiple classifier options and the appropriate classifier can be selected based on the confusion matrix output, which is a well-known tool in WEKA. Confusion matrix is a specific table layout that allows visualization of the performance of an algorithm. The confusion matrix makes it easy to see if the system is reliably classifying the different classes.

In the present invention, a variation of the nearest neighbor classifier is used to distinguish different activities. The first step in this method is to analyze the range of each attribute for all the activities. An attribute is considered as a good attribute for a classifier if there is no overlap in attribute values among different activities. Usually this condition is difficult to satisfy, as there will be always some outliers (or samples) that would tend to blur the gap between any two activities. Given this fact, the attributes with the minimum overlap on value ranges of all activities are selected as good attributes.

Figure 9:
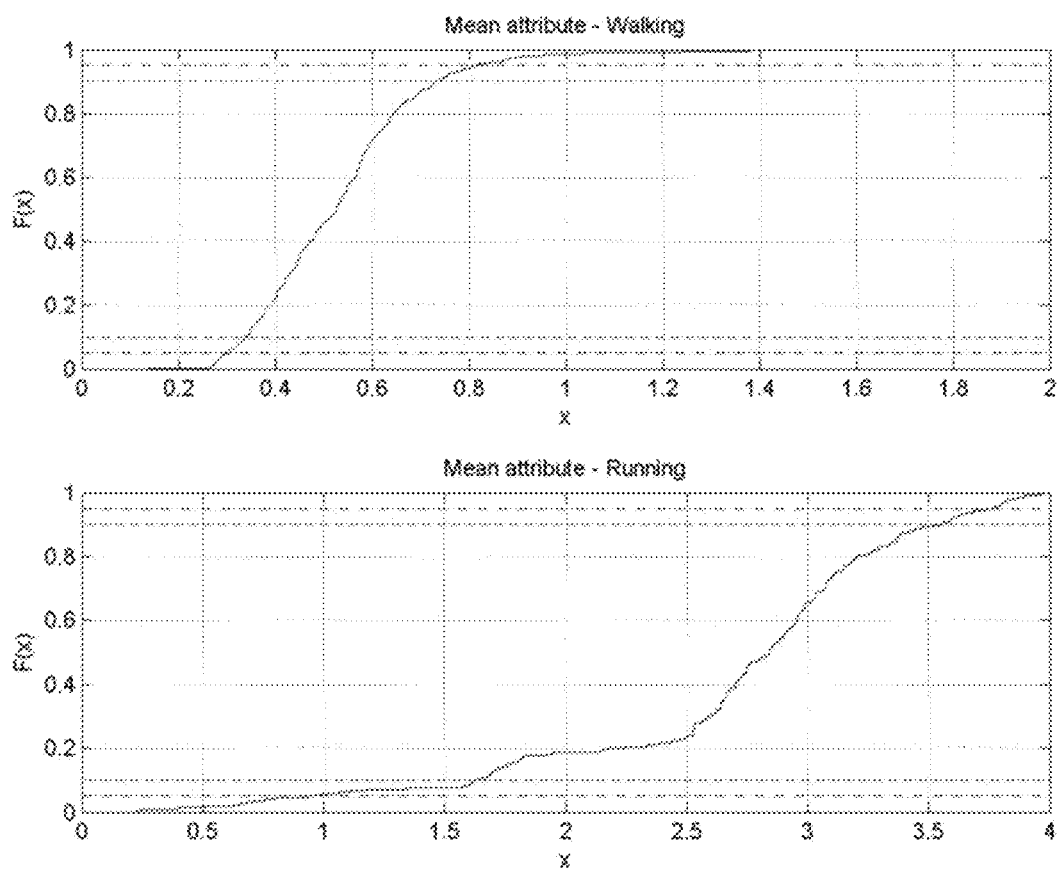
FIG. 9 illustrates an exemplary CDF (cumulative distribution function) plot of the mean attribute for walking activity and an exemplary CDF plot of the mean attribute for running activity.

For each potential attribute, the distribution of the values are detected and divided into five sections according to one example of the present invention. The range of attribute values that corresponds to the 5%, 10%, 90%, 95% and 99% of all the attribute values is determined for one particular activity. For example, FIG. 9 shows the cumulative distribution function (CDF) plot of the mean of the combined accelerometer data $\bar{m}$ for walking and running activities. The attribute values corresponding to the different activity sections (also referred to as windows) are listed in Table 1. It can be seen that the attribute value ranges for the two activities are different. There is only a small overlap on value ranges of $\bar{m}$ and therefore the attribute can be used to identify the corresponding activity. However, there are few instances where there is an overlap between these activities and in these instances the particular attribute is not useful in separating walking from running activity. Therefore, another attribute can be considered for either providing better classification than this attribute or improving the reliability when used together with this attribute.

TABLE 1

Mean of the combined accelerometer data $\bar{m}$ for walking and running activities

|  | 5% | 10% | 90% | 95% | 99% |
| --- | --- | --- | --- | --- | --- |
| $\bar{m}$ for Walking | 0.30 | 0.34 | 0.73 | 0.81 | 1.24 |
| $\bar{m}$ for Running | 0.97 | 1.63 | 3.55 | 3.74 | 3.96 |

In the algorithm according to the present invention, a subset of attributes is used and combined by using section dependent weights. The weights are configurable and can be adjusted dynamically as desired.

In the interest of simplicity, the algorithm steps are described by using the values in Table 1. Variables walk_metric and run_metric are defined to store the combined metric for walking and running activities respectively. As mentioned earlier, section dependent weights are defined corresponding to the five sections in the CDF plot. The section dependent weights are denoted as wt5, wt10, wt90, wt95 and wt99 corresponding to the (0, 5%], (5%, 10%], (10%, 90%], (90%, 95%], (95%, 99%] sections respectively.

In the case of test data, the mean of the combined accelerometer data $\bar{m}$ is computed and the following equations are used to compute or update the metrics:

$$\text{walk\_metric} = wt5*(0 < \bar{m} \leq 0.30) +$$
$$wt10*(0.30 < \bar{m} \leq 0.34) + wt90*(0.34 < \bar{m} \leq 0.73) +$$
$$wt95*(0.73 < \bar{m} \leq 0.81) + wt99*(0.81 < \bar{m} \leq 1.24)$$

$$\text{run\_metric} = wt5*(0 < \bar{m} \leq 0.97) + wt10*(0.97 < \bar{m} \leq 1.63) +$$
$$wt90*(1.63 < \bar{m} \leq 3.55) +$$
$$wt95*(3.55 < \bar{m} \leq 3.74) + wt99*(3.74 < \bar{m} \leq 3.96)$$

$$\text{Where } (m_1 < \bar{m} \leq m_2) = \begin{cases} 1 & \text{if } (m_1 < \bar{m} \leq m_2) \\ 0 & \text{otherwise} \end{cases}$$

When other attributes are used in the classifier, then the corresponding metrics are combined or added for all the attributes. Similarly, the metrics for the other activities should also be computed when the classifier is designed to identify other activities. Finally, the metrics are compared with each other and the activity is determined based on whichever has the higher values. If the metrics are equal, the activity is determined randomly (with uniform distribution) between the activities.

Different variations of the classifier 170 can be used to adapt the algorithm according to the requirements. For example, more sections can be used if finer resolution is required.

In one embodiment according to the present invention, four attributes are used which are namely, the mean of combined accelerometer data $\bar{m}$, time domain energy of the combined accelerometer data $E_{TD}$, variance of vertical component $var_v$ and Sub-band frequency domain energy $E_{FD}$.

Figure 10:
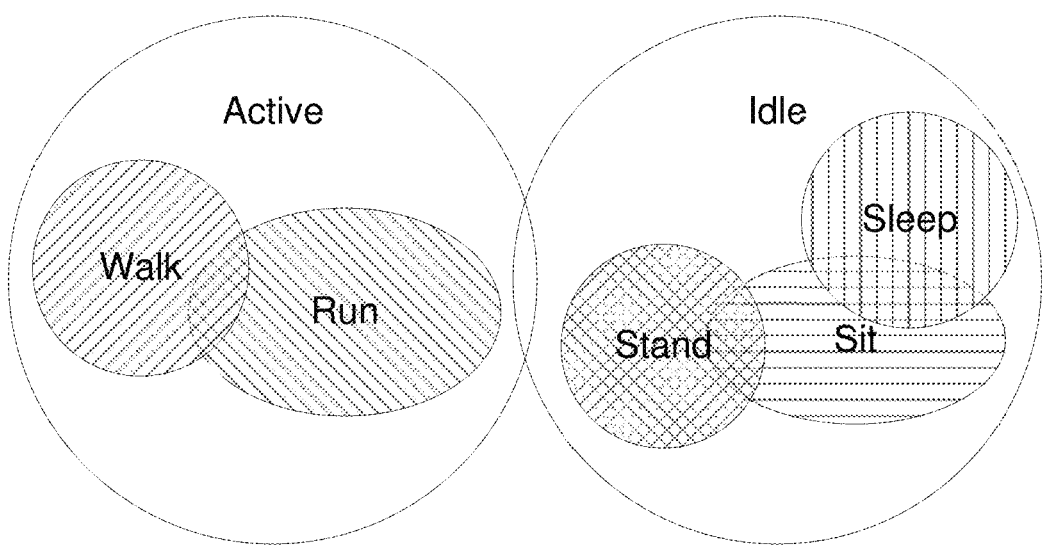
FIG. 10 illustrates an exemplary successive classification for activity tracking.

Successive classification approach can be used if some of the activities to be classified have similar characteristics. For example as shown in FIG. 10, in the case of user activity, sitting and standing activities can be grouped into one class referred to as idle. Similarly, user activities of walking, running and jumping can be grouped into another class referred to as active. The classifier can be designed to classify user activities in two stages. The classifier will classify the activity into idle and active in the first stage and then in the second stage the classifier will sub-classify the activity identified within idle or active. The successive classification approach provides flexibility in allocating computational resources, meeting latency requirements and improving the performance.

In one example, a MCU (microcontroller unit) is used for the implementation of the algorithms of the classifier 170 and the step counter 160, and part of the system state machine control as well. Most of the burden comes from activity detection and step counting which require large number of multiplication and addition operations. In the following paragraphs, some implementation details are presented on the classifier 170.

The classifier 170 provides real-time information of the current activity status by using a specific classifier algorithm, such as a decision making tree, a SVM (support vector machine) or a logistics method. Attribute selection and calculation is the key of the classifier 170 to get accurate activity detection. Each attribute reflects an inherent characteristic of an activity that is statistically different from other activities.

According to one embodiment of the present invention, three significant attributes are selected in the designed classifier, namely the mean value, time domain energy of filtered data excluding DC component, and variance of the dominant component (vertical or horizontal component). Experiments show the effectiveness of these three attributes with as high as 95% accuracy in classification. The classifier is chosen as decision making tree method and marked as J.48 in WEKA software, which is very simple in the algorithm implementation. The classifier described in previous sections, which states how to derive classifier and the successive classification approach, is also implemented and can be enabled by the user.

Figure 11:
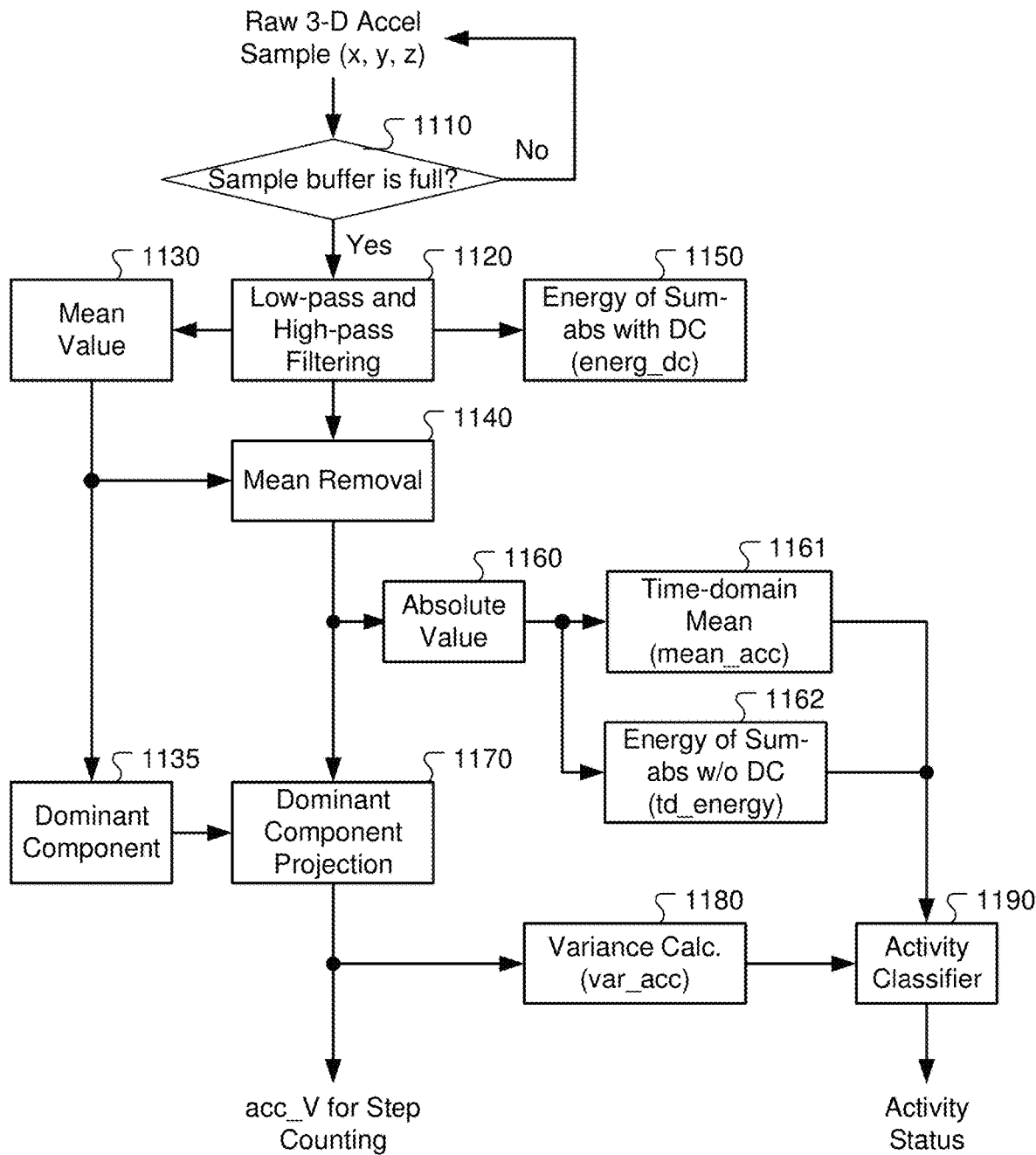
FIG. 11 illustrates an exemplary flowchart of activity detection according to the present invention.

These three significant attributes are calculated for the activity detector. FIG. 11 shows the sample flowchart of the activity detector. In this example, data processing is blockwise where the size of sample buffer is 128 corresponding to 2.56 seconds at 50 Hz sampling rate. The raw 3-D accelerometer sample (x, y, z) is stored in a sample buffer. The status of the sample buffer is determined in step 1110. When the sample buffer is full, the pre-processor is applied to filter out the high-frequency signals and noise signals in the band out-of-interest in step 1120. The mean value is calculated in step 1130 and subtract from the filtered 3-D data in step 1140. Then the abs(.) operation is performed in step 1160 on the filtered 3-D data. Then two attributes used for activity detection, which are the time domain mean value (mean_acc) and the time domain energy (td_energy) without DC component, are estimated in step 1161 and step 1162.

Based on the mean value in x, y, and z direction, normalization is performed to obtain a unit vector indicating dominant component direction with most signal energy. The dominant component is computed in step 1135. Projecting the 3-D data excluding DC component on dominant component vector will generate acc_V in step 1170. The dominant component acc_V is also the input of the step counter module. The third attribute is the variance of acc_V, which is extracted as var_acc in step 1180. By using activity classifier, the current activity status is determined in step 1190 based on these three attributes.

If the activity detection is also based on frequency domain processing, the frequency domain attributes are also provided to the activity classifier. The frequency domain attributes may be calculated based on the combined accelerometer data. The frequency domain attributes may be also derived in the transform domain step counter module. Thus, the frequency domain transformation is performed after step 1170, and the frequency domain attributes are extracted from the vertical component or the horizontal component.

The classification rules are obtained by the training from data capture sets including different known activity status, such as idle and active modes. Idle status contains sub-class of standing and sitting, whereas active modes includes slow walking, normal walking, fast walking, running, jumping, climbing up, climbing down and so on. In classifier training stage, the input to the classifier include the pre-defined attributes and activity status for each training sample belonging to a specific activity, the output is the classification rules used for classifying new data captures.

Figure 12:
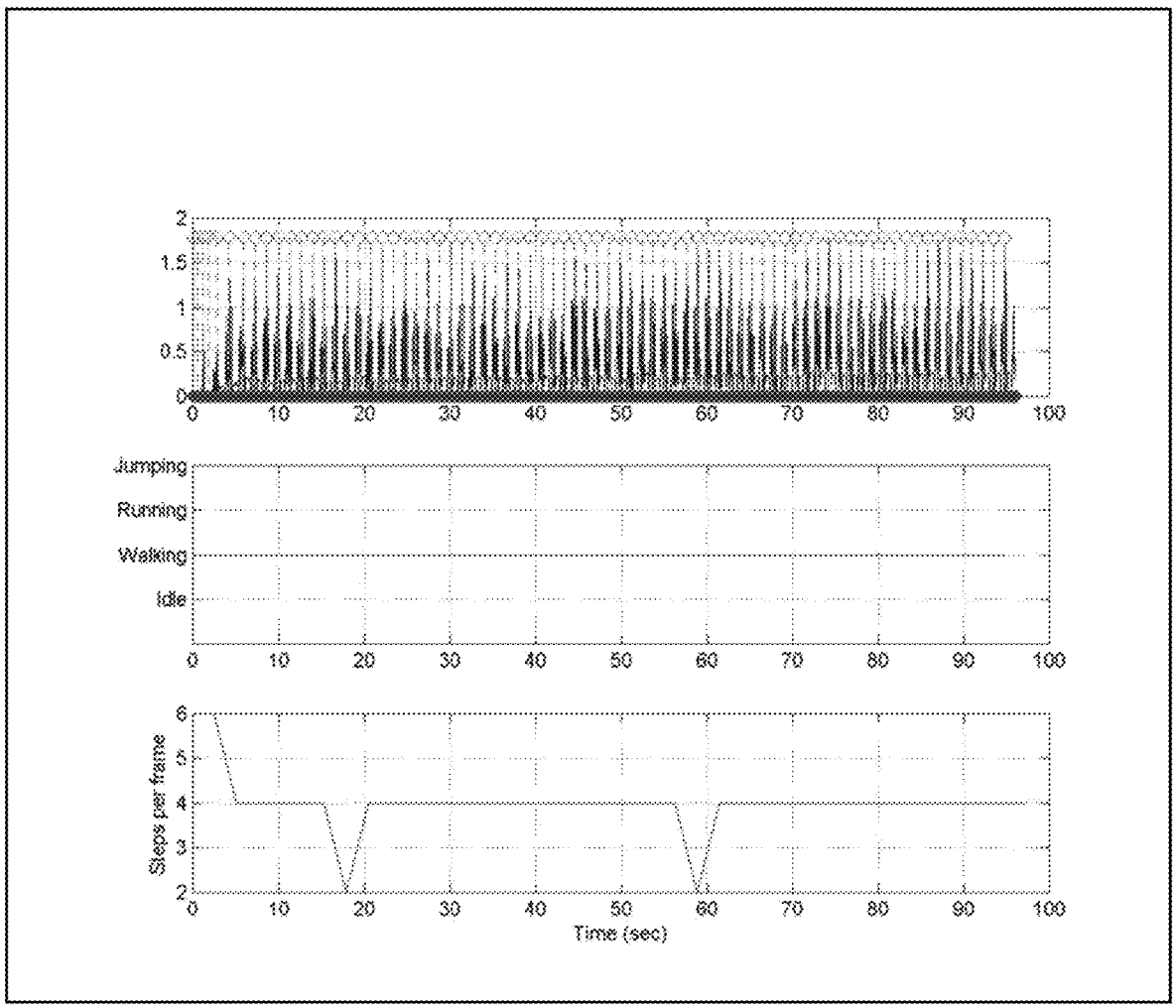
FIG. 12 illustrates an example of the activity detector performance for walking activity with the sensor on the shoe.
Figure 13:
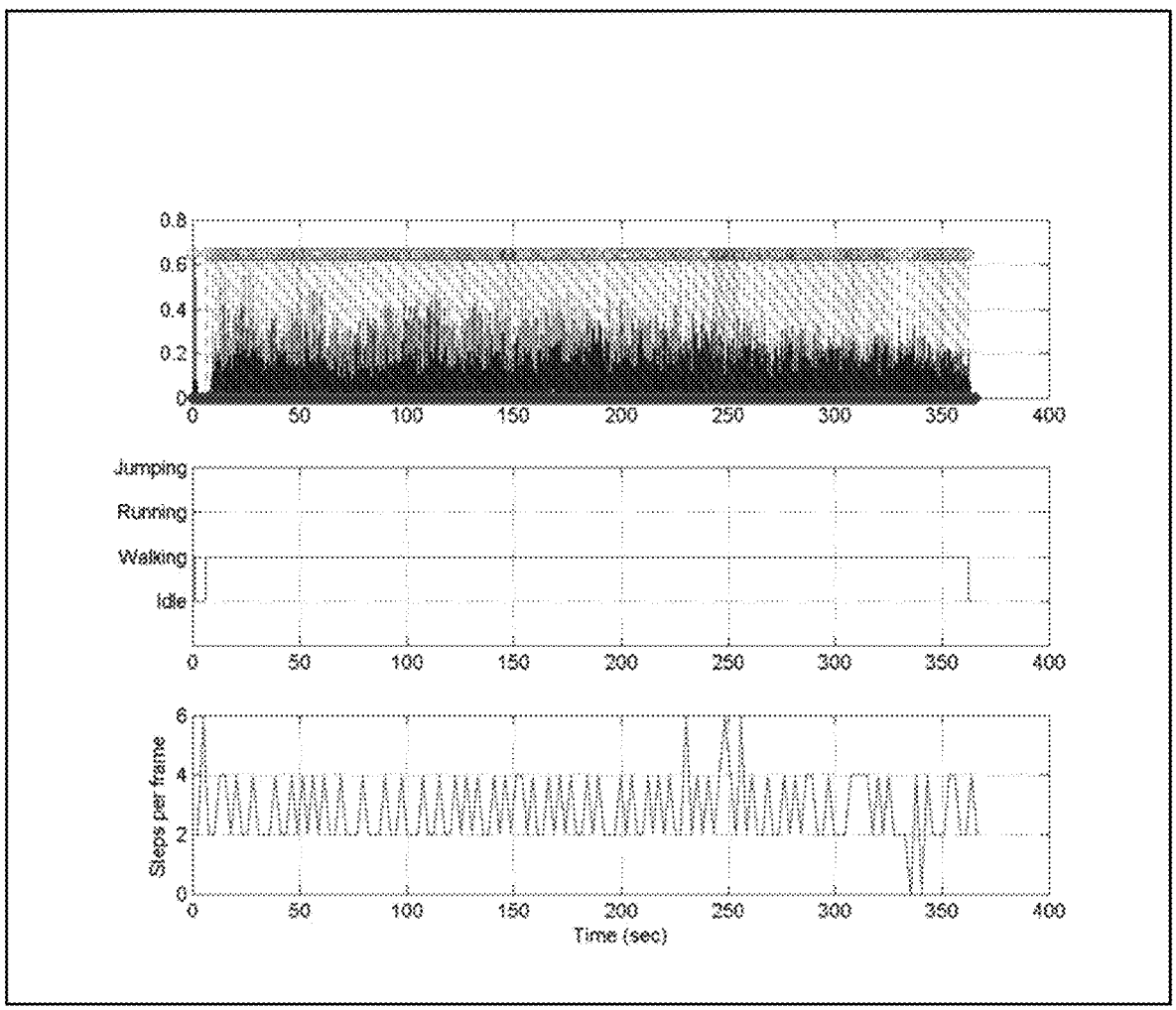
FIG. 13 illustrates an example of the activity detector performance for walking activity with the sensor on the wrist.

In some embodiments, the accuracy of activity tracking can be significantly improved. FIG. 12 and FIG. 13 show the performance of the activity detector for one sample data log of walking activity with sensor placed on one shoe and on one wrist respectively. The middle plot in these two figures shows the estimated activity and the floating-point result corresponds very well with the logged activity information.

Figure 14:
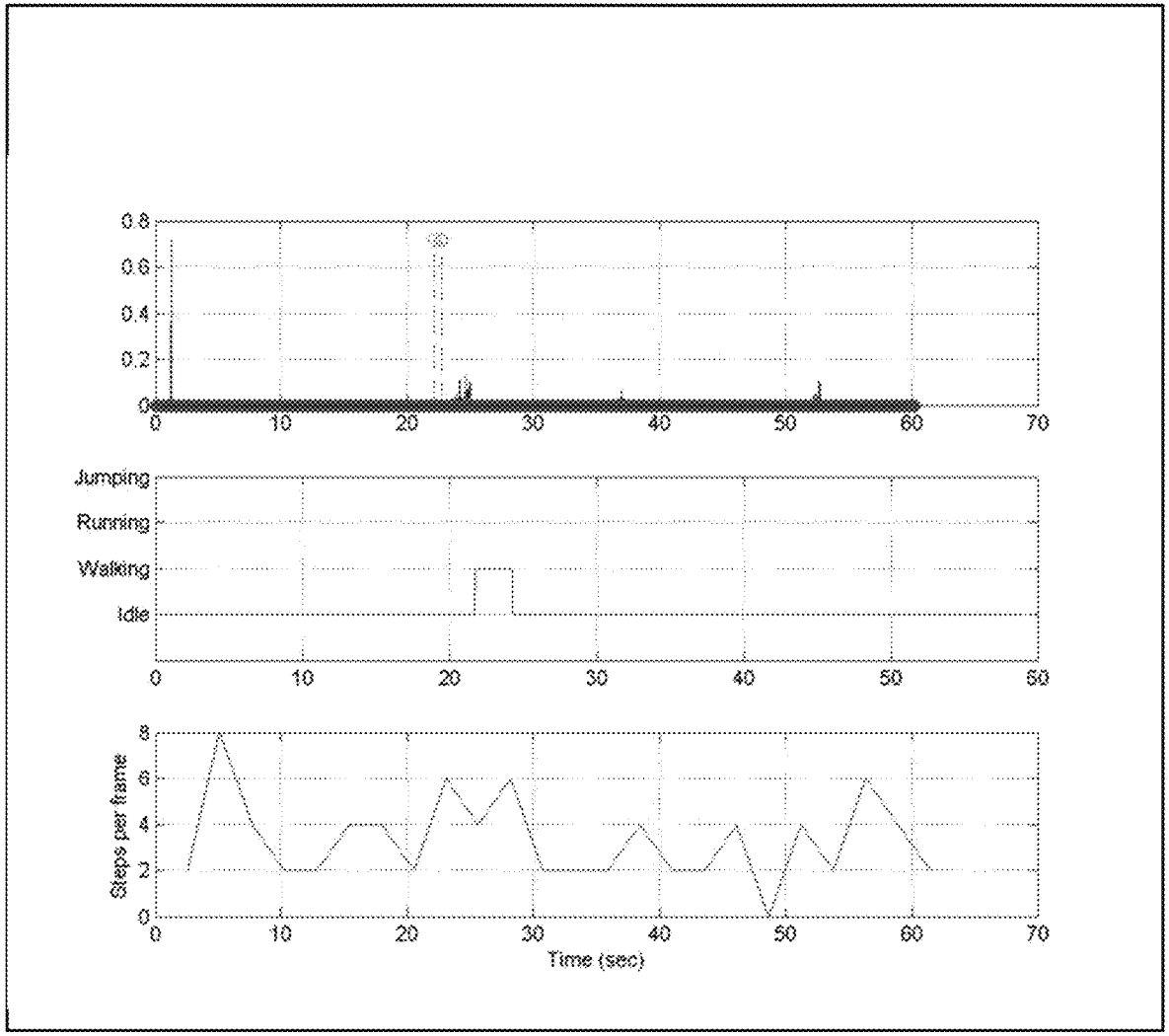
FIG. 14 illustrates an example of the activity detector performance for sitting activity with the sensor placed on the shoe.
Figure 15:
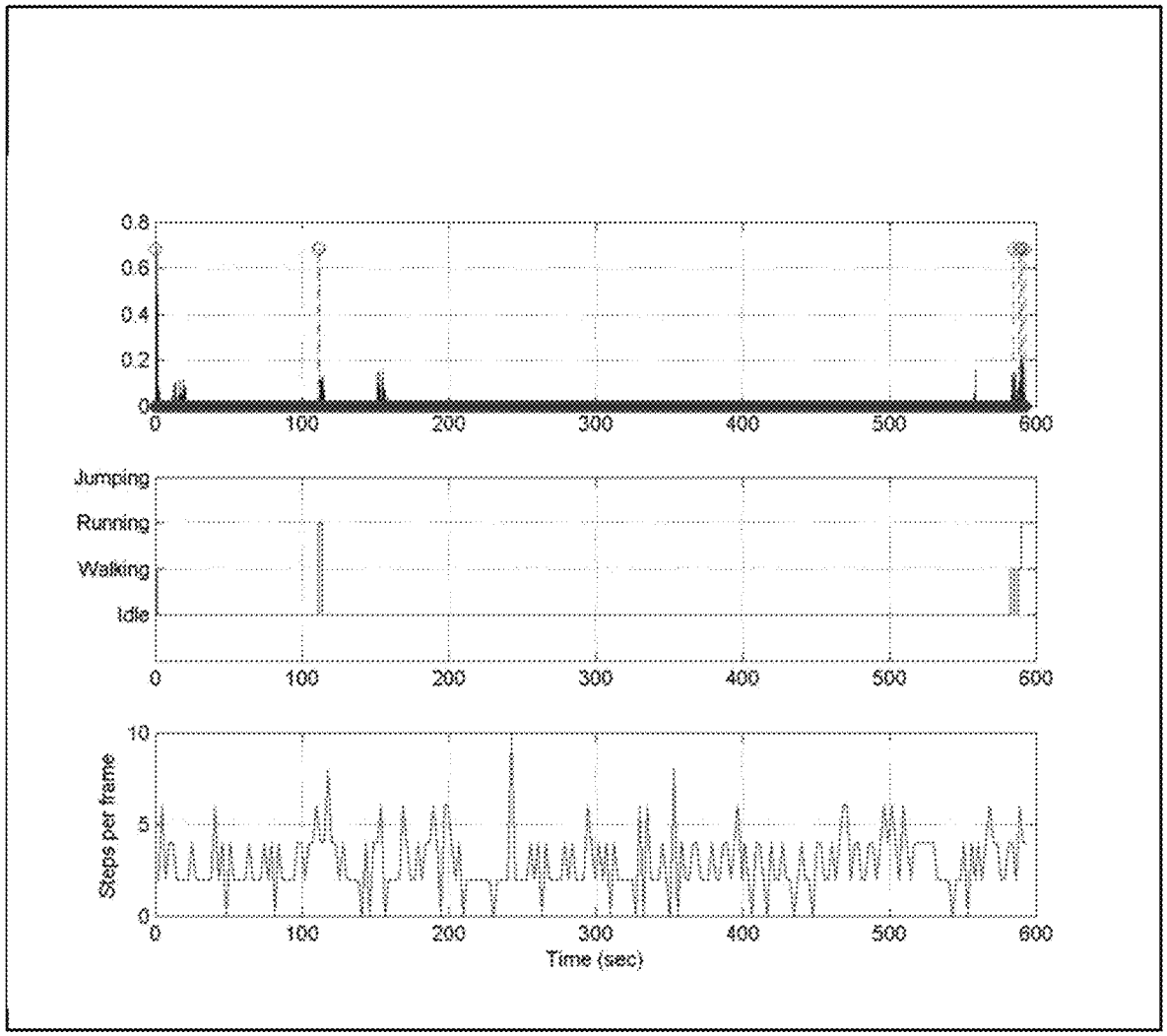
FIG. 15 illustrates an example of the activity detector performance for sitting activity with the sensor on the wrist.

FIG. 14 and FIG. 15 show the performance of the activity detector for sitting activity with sensor placed on one shoe and one wrist respectively. The floating-point result also corresponds very well with the logged activity information.

In fixed-point algorithm, all multiplication operation is implemented using 32-bit representation according to one embodiment of the present invention.

Figure 16:
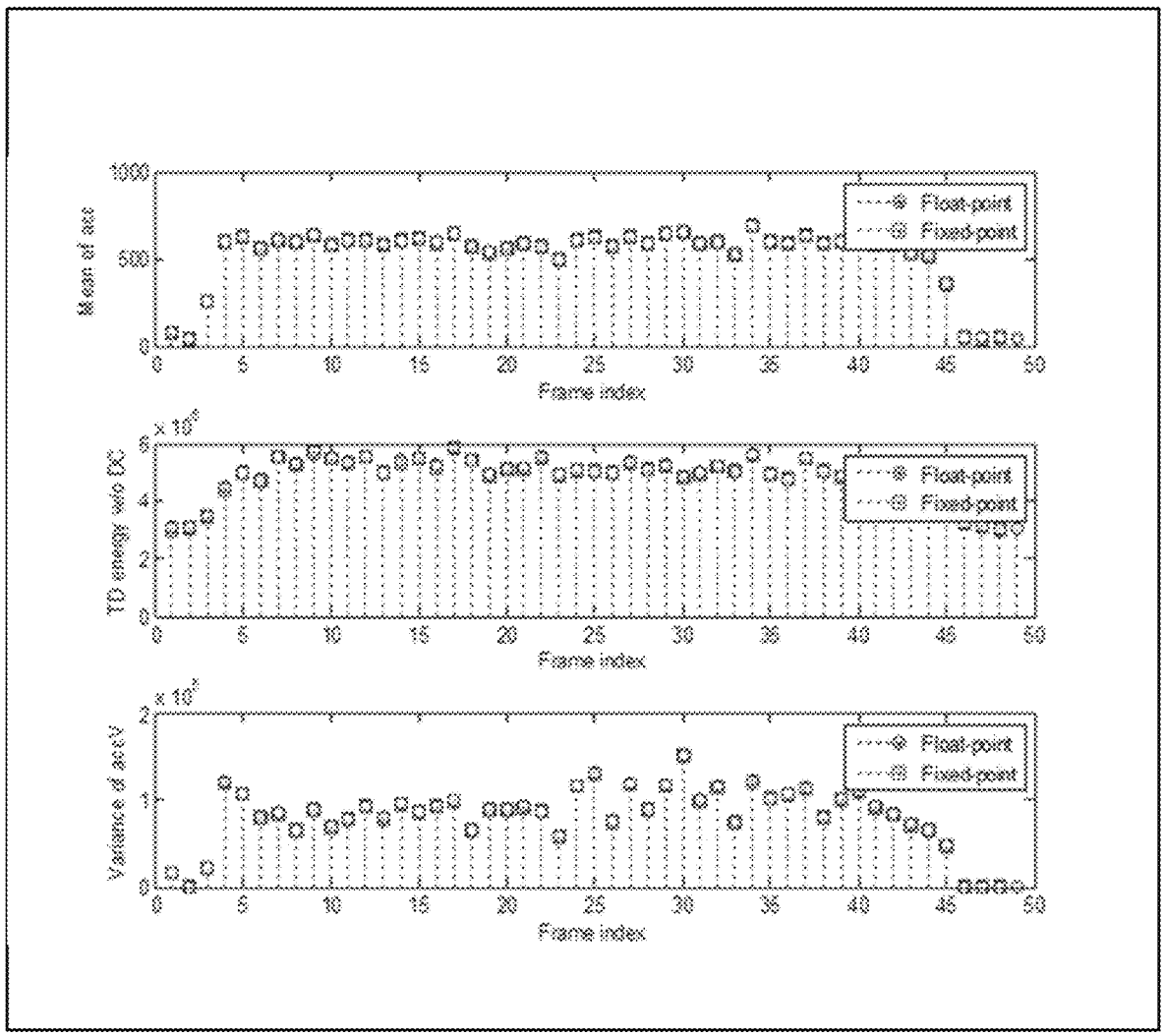
FIG. 16 illustrates an example of comparing three attributes used for activity classification for normal walking activity with the sensor on the wrist.
Figure 17:
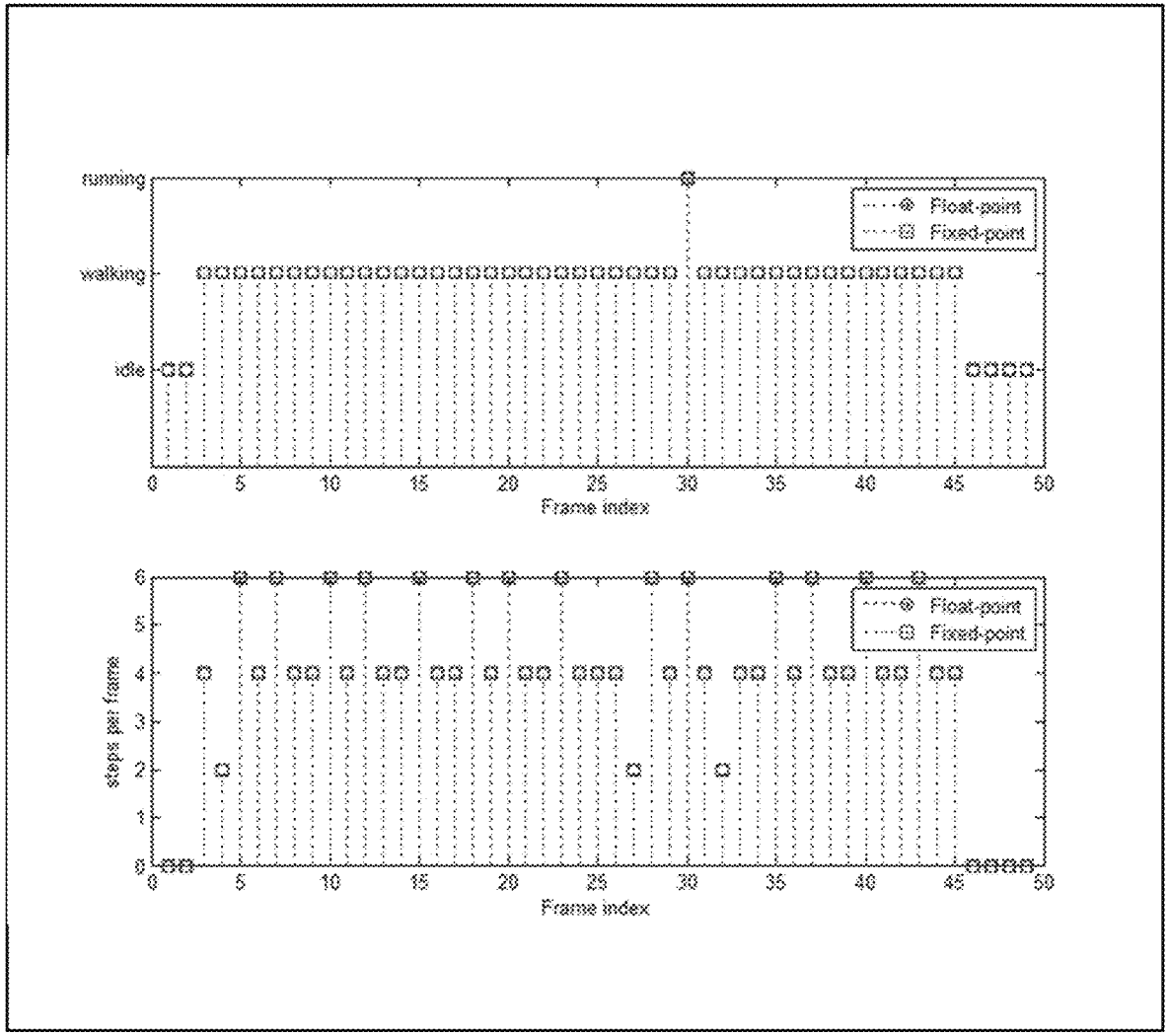
FIG. 17 illustrates an example of comparing activity detector and step count performance for normal walking activity with the sensor placed on the wrist.
Figure 18:
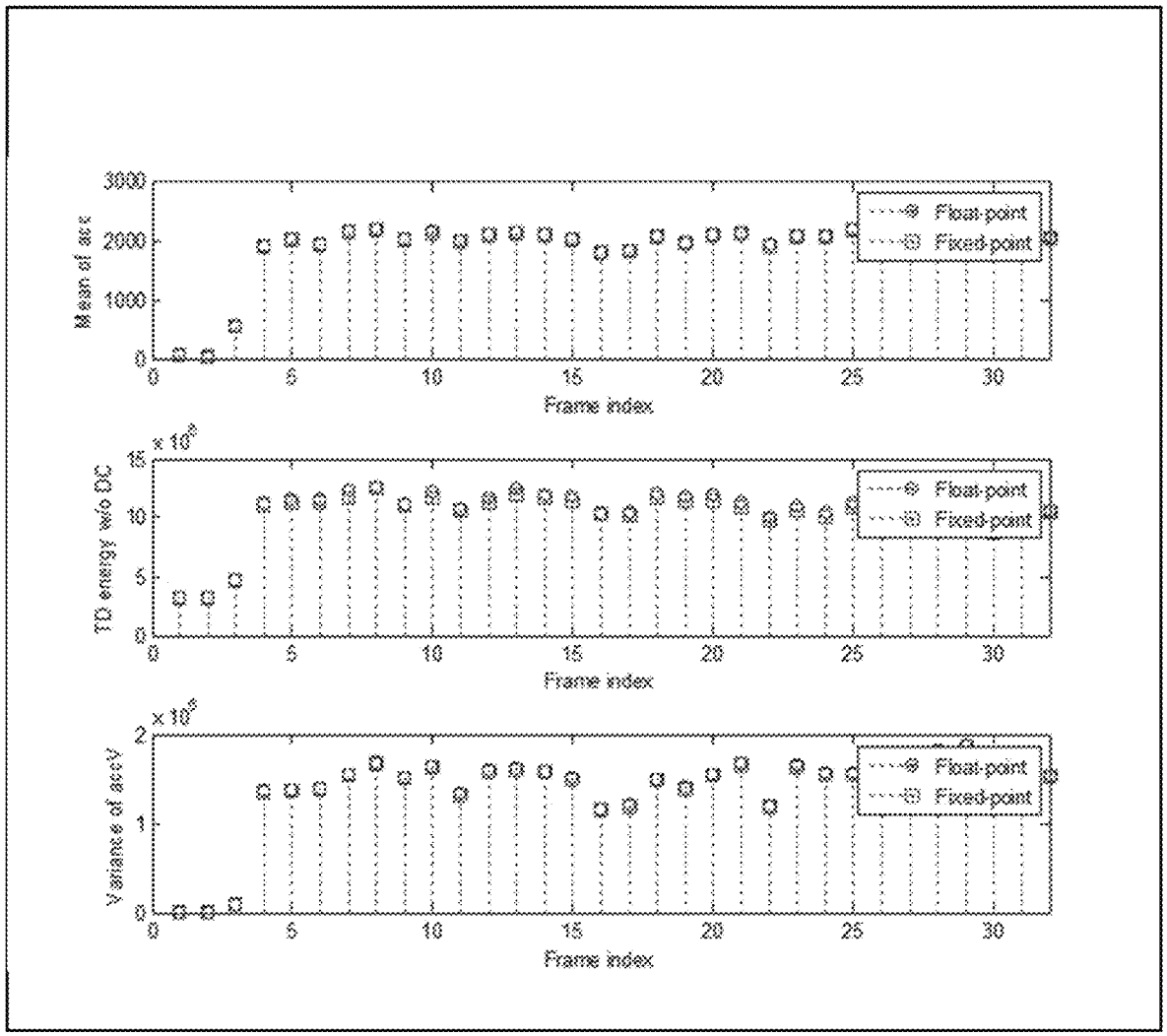
FIG. 18 illustrates an example of comparing three attributes used for activity classification for running activity with the sensor placed on the wrist.
Figure 19:
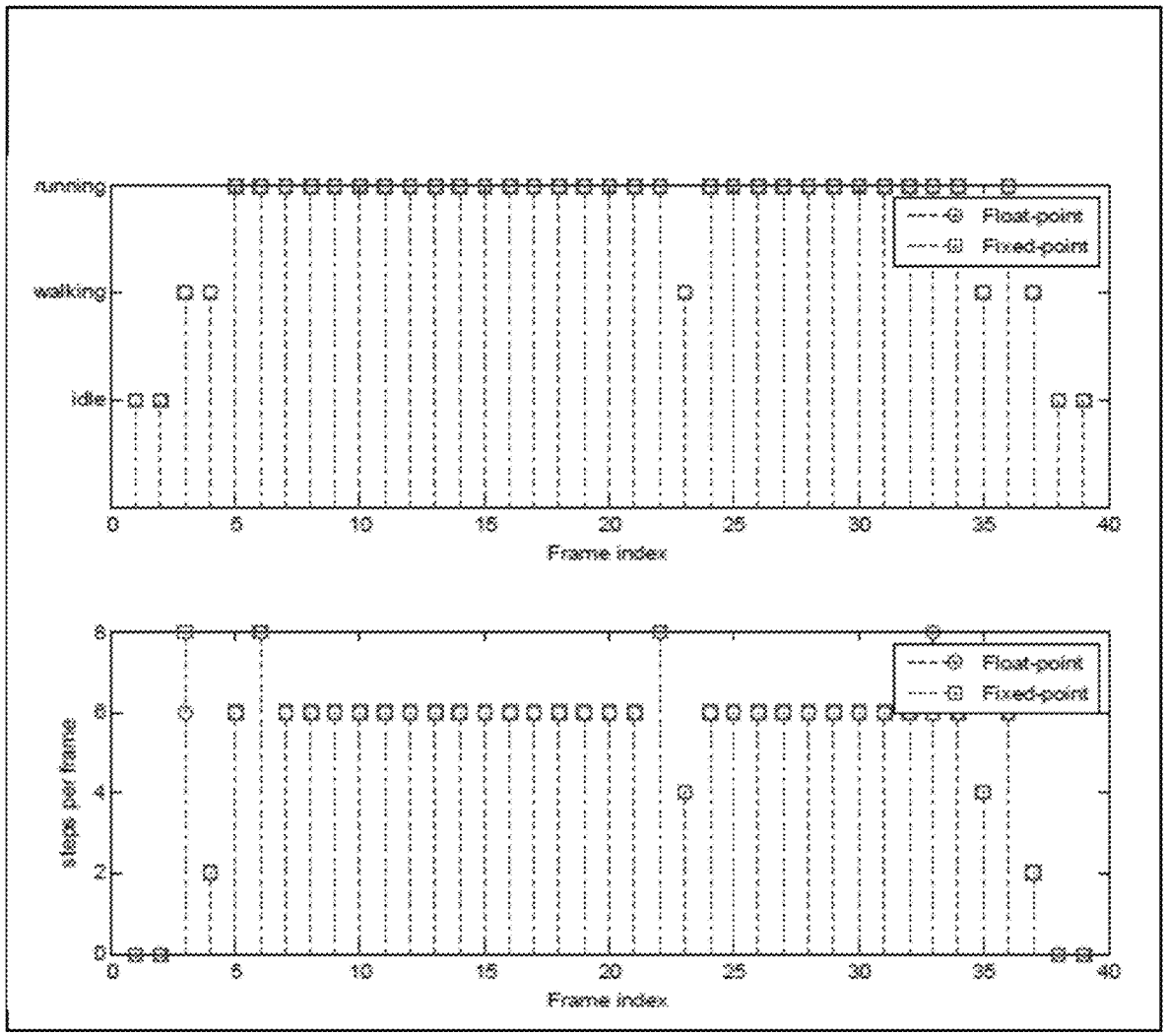
FIG. 19 illustrates an example of comparing activity detector and step count performance for running activity with the sensor placed on the wrist.

In some embodiments, the output of the fixed-point implementation is also compared with that of the floating-point implementation. FIG. 16 illustrates an example of comparison for three attributes based on the walking data from a wrist sensor. FIG. 17 illustrates an example of comparison for activity detection and step counting based on the data from a wrist sensor. FIG. 18-19 presents similar plots for running activity with a wrist sensor. It can be observed that for both walking and running, there is a very good match between the fixed point and floating point simulations.

The above description is presented to enable a person of ordinary skill in the art to practice the present invention as provided in the context of a particular application and its requirement. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In the above detailed description, various specific details are illustrated in order to provide a thorough understanding of the present invention. Nevertheless, it will be understood by those skilled in the art that the present invention may be practiced.

The invention claimed is:

1. A system for activity tracking, the system comprising:
   a 3-dimensional (3-D) accelerometer configured to sense activity in each of three orthogonal axes being X-axis, Y-axis and Z-axis, and generating accelerometer data associated with the three axes;
   a pre-processor coupled to the 3-D accelerometer and including a filter circuit configured and arranged to remove noise from the accelerometer data and, therefrom produce filtered data including vertical and horizontal component data and accelerometer data associated with each of the three axes; and
   a computer processor configured and arranged with previously-obtained statistical data indicative of a plurality of attributes of each different activity classes characterizing movement of a user and with programming instructions which when executed, the computer processor performs operations to identify, independent of orientation of the 3-D accelerometer, one of the different activity classes corresponding to produced accelerometer data, the operations including the following:
      deriving, from the filtered data, values associated with activity-indicative attributes including mean value, time domain energy of filtered data, and variance of the vertical and horizontal component data,
      processing and comparing each of the values of the activity-indicative attributes with the previously-obtained statistical data to classify the produced accelerometer data as corresponding to a selected current activity from among the different activity classes, and
      tracking and characterizing the tracked data as the selected current activity of one of the different activity classes, wherein the selected current activity corresponds with the movement of the user.

2. The system of claim 1, wherein the filter is further configured and arranged to remove direct current (DC) component from the accelerometer data.

3. The system of claim 1, wherein the computer processor is further configured to, in response to tracking and characterizing the tracked data as the selected current activity, log activity of the user associated with the different activity classes over a period of time and provide performance data indicative of the logged activity including the tracked data characterized as the selected current activity.

4. The system of claim 1, wherein the computer processor is further configured to determine which of the vertical component and the horizontal component is dominant based on an amount of energy indicated the vertical component and the horizontal component and to characterizing the tracked data as the selected current activity based on a variance of the dominant one of the vertical component and the horizontal component.

5. The system of claim 1, wherein the pre-processor is configured to produce the filtered data including vertical and horizontal component data and accelerometer data associated with each of the three axes independent of the orientation of the 3-D accelerometer.

6. A non-transitory computer readable media including programming instruction which when executed by a computer processor performs the following operations:
continuously sensing, using a 3-dimensional (3-D) accelerometer, activity in each of three orthogonal axes being X-axis, Y-axis and Z-axis corresponding with movement of a user;
pre-processing accelerometer data which is output from the 3-D accelerometer, wherein the pre-processing includes causing the data which is output from the 3-D accelerometer to be filtered by removing noise and removing a direct current (DC) component from an output of the 3-D accelerometer;
deriving, after the pre-processing, a vertical component and a horizontal component of the output of the 3-D accelerometer, wherein the vertical component is proportional to a vector inner product between a mean vector of a plurality of vector samples along the three axes and each vector corresponding to a first difference between each of the plurality of vector samples and the mean vector, wherein the horizontal component is related to a norm of a second difference between the first difference and the mean vector scaled by the vertical component;
determining which of the vertical component and the horizontal component indicates an amount of energy that is greater than an amount of energy indicated by the other of the vertical component and the horizontal component; and
determining, tracking and characterizing an activity type from a plurality of activity types characterizing the movement of the user, independent of orientation of the 3-D accelerometer and based on statistical data corresponding to the output of the 3-D accelerometer and the vertical component or the horizontal component having the greater amount of energy.

7. The computer readable media of claim 6, further including determining the activity type based on a step counting, wherein the step counting is calculated based at least partly on the vertical component or the horizontal component having the greater amount of energy.

8. The computer readable media of claim 6, wherein the statistical data includes:
at least one of a time domain mean value, a variance, a signal energy of the vertical component or the horizontal component having the greater amount of energy;
a first set of statistical data generated based on the pre-processing; and
a second set of statistical data generated based on the determining whether the vertical component or the horizontal component has the greater amount of energy.

9. The computer readable media of claim 6, wherein determining the activity type is further based on cumulative distribution for first values of the statistical data, wherein the cumulative distribution is divided into multiple sections associated with first values of the statistical data and second values of a plurality of statistical features of a particular activity, and wherein each section corresponds to a ratio range of the first values to the second values.

10. The computer readable media of claim 6, wherein determining the activity type is further based on cumulative distribution for first values of the statistical data, wherein the cumulative distribution is divided into multiple sections associated with first values of the statistical data and second values of a plurality of statistical features of a particular activity, and wherein each section corresponds to a ratio range of the first values to the second values as follows: great than 0 and equal to or less than 5%, great than 5% and equal to or less than 10%, great than 10% and equal to or less than 90%, great than 90% and equal to or less than 95%, and great than 95% and equal to or less than 99%.

11. The computer readable media of claim 6, wherein determining, tracking and characterizing the activity type from the plurality of activity types further includes determining which of the vertical component or the horizontal component are a dominant component responsive one of the vertical component or the horizontal component having the greater amount of energy, and characterizing the activity type based on a variance of the dominant component.

12. The computer readable media of claim 6, wherein in response to determining, tracking and characterizing the activity type, the operations further include logging activity of the user associated with the activity type and providing performance data indicative of the logged activity to the user.

13. A computer readable media including programming instructions which when executed by a processor performs an operation for determining an activity from a set of multiple possible activities, the operation includes:
sensing, using a 3-dimensional (3-D) accelerometer, activity in each of three orthogonal axes being X-axis, Y-axis and Z-axis corresponding with movement of a user;
receiving raw data from the 3-D accelerometer;
causing the raw data to be filtered by removing noise and removing a direct current (DC) component from the raw data;
calculating a time domain mean value and a time domain energy of the filtered raw data;
estimating a component in the filtered raw data having a greatest amount of energy; and
determining, tracking and characterizing the activity characterizing the movement of the user, independent of orientation of the 3-D accelerometer and based on the estimated component and the time domain mean value and the time domain energy.

14. The computer readable media of claim 13, wherein the operation further includes calculating the time domain mean value prior to the estimating.

15. The computer readable media of claim 13, wherein determining, tracking and characterizing the activity characterizing the movement of the user, further includes identifying a variance of the estimated component, and determining the activity based on the variance of the estimated component and the time domain mean value and the time domain energy.

16. The computer readable media of claim 13, the operation further including determining, tracking and characterizing activity characterizing movement of the user corresponding to a plurality of activities from the set of multiple possible activities over time, logging activity of the user associated with the plurality of activities and providing performance data indicative of the logged activity to the user.

* * * * *